(12) United States Patent
Furukawa et al.

(10) Patent No.: US 11,337,882 B2
(45) Date of Patent: May 24, 2022

(54) PATTERN CHANGING SHEET, WALKING GUIDANCE SYSTEM, AND MOVING SPEED REDUCTION DEVICE

(71) Applicant: OSAKA UNIVERSITY, Osaka (JP)

(72) Inventors: Masahiro Furukawa, Osaka (JP); Nobuhito Sakamoto, Osaka (JP); Taro Maeda, Osaka (JP)

(73) Assignee: Osaka University, Osaka (JP)

( * ) Notice: Subject to any disclaimer, the term of this patent is extended or adjusted under 35 U.S.C. 154(b) by 455 days.

(21) Appl. No.: 16/671,496

(22) Filed: Nov. 1, 2019

(65) Prior Publication Data

US 2020/0060920 A1 Feb. 27, 2020

Related U.S. Application Data

(63) Continuation of application No. PCT/JP2018/018082, filed on May 10, 2018.

(30) Foreign Application Priority Data

May 12, 2017 (JP) ................................ JP2017-95606

(51) Int. Cl.
*A61H 3/00* (2006.01)
*G02B 26/02* (2006.01)
*A61B 5/11* (2006.01)

(52) U.S. Cl.
CPC ............ *A61H 3/00* (2013.01); *G02B 26/026* (2013.01); *A61B 5/112* (2013.01)

(58) Field of Classification Search
CPC ........ A61H 3/00; A61H 3/066; G02B 26/026; G02B 3/06; G02B 3/0056; A61B 5/112; G09B 19/00; G09F 19/12
See application file for complete search history.

(56) References Cited

U.S. PATENT DOCUMENTS 3,811,213 A * 5/1974 Eaves .................... G09F 13/00
 40/437
3,885,876 A * 5/1975 Konopka ............... B64D 45/08
 356/399

(Continued)

FOREIGN PATENT DOCUMENTS

JP 2000-172203 A 6/2000
JP 2002-272796 A 9/2002

(Continued)

OTHER PUBLICATIONS

International Search Report for corresponding Application No. PCT/JP2018/18082, dated Jul. 17, 2018.
Hiromi Yoshikawa, Vection Field_the Visual Navigation Method for Pedestrian, Information Processing Society of Japan, Interaction 2011 (with English Abst.).
Masahiro Furukawa, Hiromi Yoshikawa, Taku Hachisu, Shogo Fukushima, Hiroyuki Kajimoto, "Vection Field" for Pedestrian Traffic Control, Augmented Human international conference, 2011 (Tokyo, Mar. 12-14, 2011).

(Continued)

*Primary Examiner* — Bryan Earles
(74) *Attorney, Agent, or Firm* — Renner, Otto, Boisselle & Sklar, LLP

(57) ABSTRACT

A pattern changing sheet includes: lenticular lenses in number corresponding to one wavelength of the pattern changing sheet and disposed with the bus-line pitch to in the direction orthogonal to the optical axis; and a pattern layer opposed to the lenticular lenses on the rear face of the lenticular lenses, the pattern layer having a gradation pattern (dots) disposed in the bus-line pitch $L_0$. The gradation pattern includes bright dots and dark dots in the bus-line pitch to in the disposing direction. The viewer views the display pattern that is a connection of the corresponding dots of the lenticular lenses depending on the viewpoint position, and the display pattern progresses at a predetermined speed scale-factor of the movement of the viewpoint. This configuration creates and provides a pattern changing sheet having a high degree of freedom and depending on the intended use.

7 Claims, 33 Drawing Sheets

(56) References Cited

U.S. PATENT DOCUMENTS

| | | | |
|---|---|---|---|
| 8,848,006 B2* | 9/2014 | Wetzstein | H04N 13/31 |
| | | | 345/679 |
| 10,282,891 B2* | 5/2019 | Han | G06T 15/08 |
| 10,321,118 B2* | 6/2019 | Park | H04N 13/139 |
| 2009/0246746 A1 | 10/2009 | Roerdink et al. | |
| 2014/0146388 A1* | 5/2014 | Kautz | G02B 30/27 |
| | | | 359/463 |
| 2017/0085867 A1* | 3/2017 | Baran | H04N 13/122 |
| 2021/0059565 A1* | 3/2021 | Morris | G06N 20/00 |

FOREIGN PATENT DOCUMENTS

| | | |
|---|---|---|
| JP | 2008-546 A | 1/2008 |
| JP | 2009-240775 A | 10/2009 |

OTHER PUBLICATIONS

Hiromi Yoshikawa, Taku Hachisu, Shogo Fukushima, Masahiro Furukawa, Hiroyuki Kajimoto and Takuya Nojima, Studies of Vection Field II: a method for generating smooth motion pattern, Advanced Visual Interfaces, International Working Conference in cooperation with ACM-SIGCHI, ACM-SIGMM, Capri Island (Naples), Italy, May 21-25, 2012 (Refereed, Poster).

Hiromi Yoshikawa, Taku Hachisu, Shogo Fukushima, Masahiro Furukawa, Hiroyuki Kajimoto, Vection Field for Pedestrian Traffic Control, ACM SIGGRAPH 2011 Emerging Technologies, Article No. 21, doi: 10.1145/2048259. 2048280, Aug. 2011.

* cited by examiner

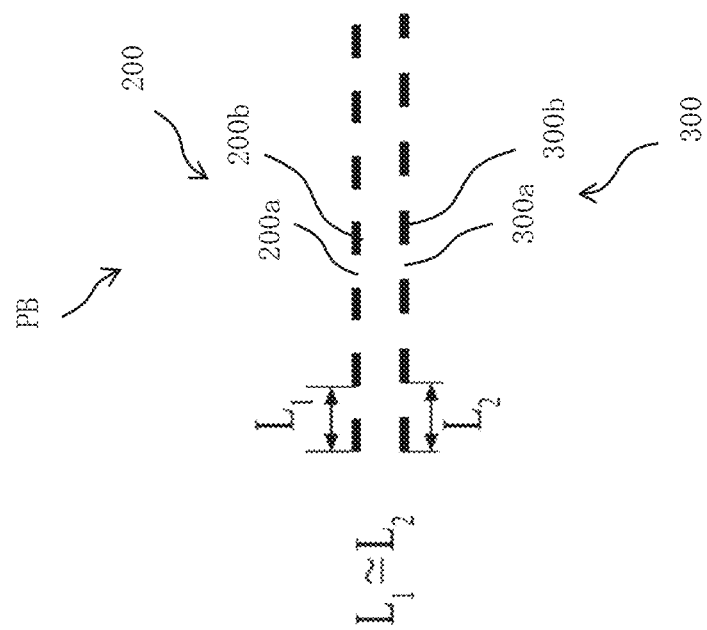

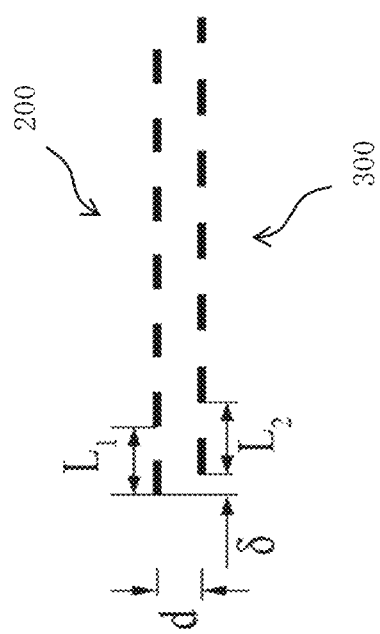

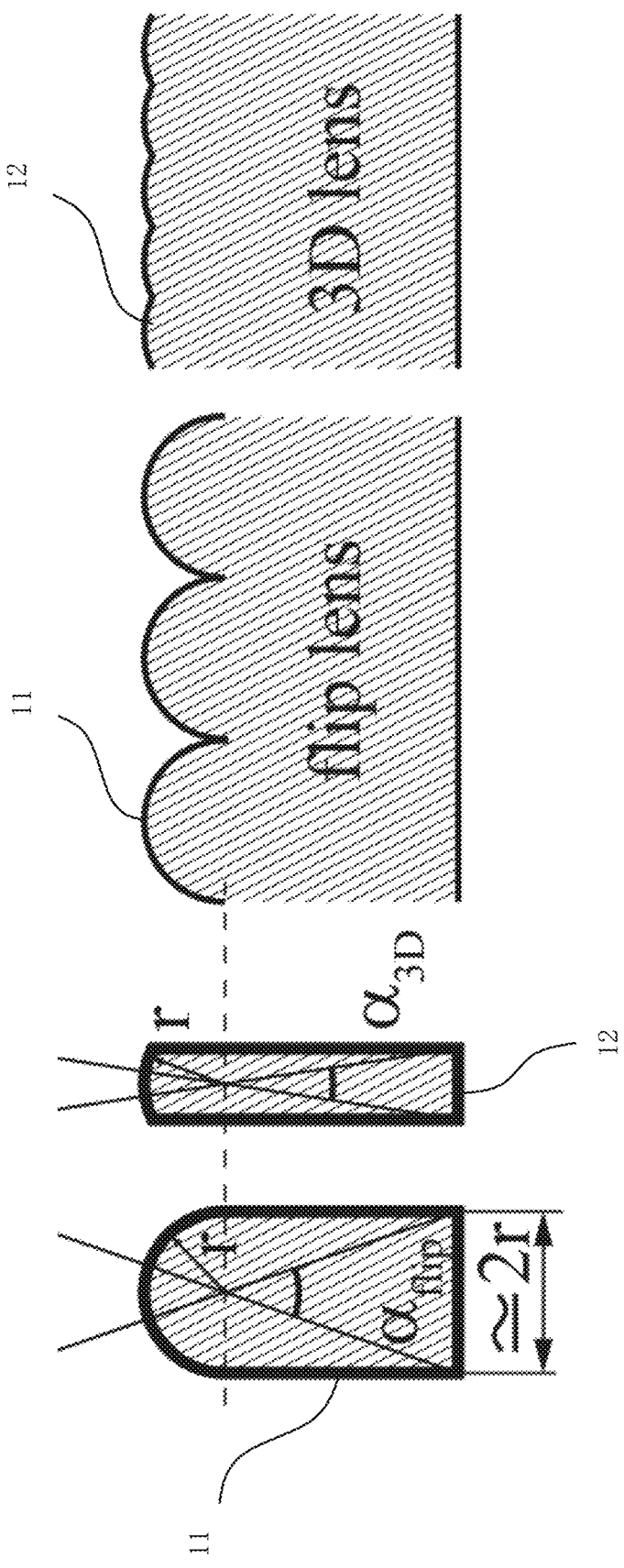

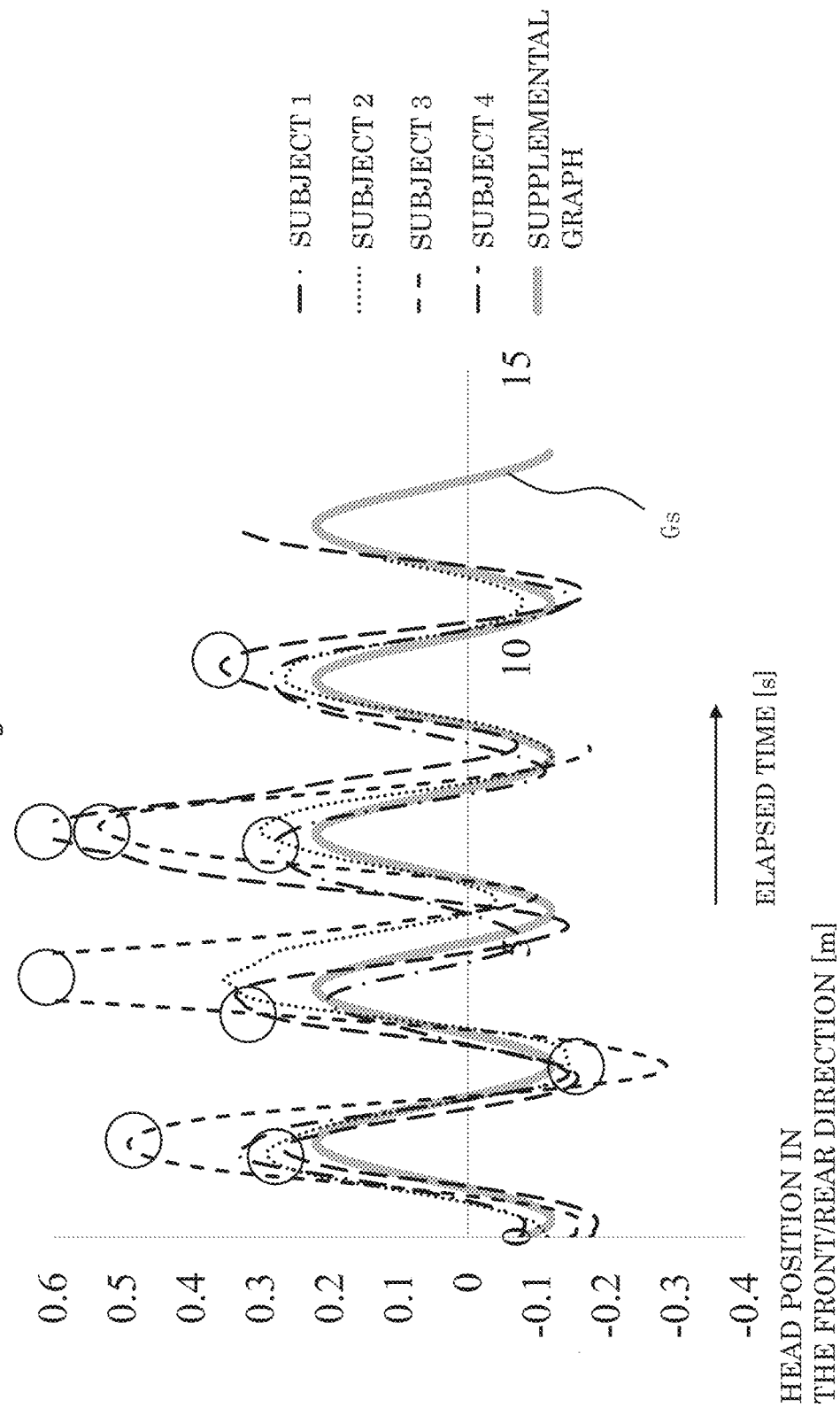

PATTERN CHANGING SHEET, WALKING GUIDANCE SYSTEM, AND MOVING SPEED REDUCTION DEVICE

BACKGROUND OF THE INVENTION

1. Field of the Invention

The present invention relates to a pattern changing sheet having a pattern that moves visually and more speedily in accordance with the moving speed of the observer's head, and a walking guidance system and a moving speed reduction device that include such a sheet.

2. Description of the Related Art

Recently display techniques have been described, which display a plurality of images while switching these images via a lenticular-lens array, and display a lot of image information effectively (JP 2000-172203 A, for example). JP 2000-172203 A proposes a visual flow pattern generator as well, which opposes a striped zebra-pattern and a lenticular-lens array that so that the displayed pattern changes at the speed Vb in accordance with the moving speed Va of the observer's head. This visual flow pattern is advantageous because it does not require the observer's burden to learn symbols and letters for cognition, and does not need energy supplied for displaying.

The visual flow pattern generator described in JP 2000-172203 A is configured so that the pitch of the convergent positions of the lenticular-lens array and an integral multiple of the gradation pitch of the zebra pattern are slightly displaced depending on the viewpoint position of the observer when the observer sees the lenticular-lens array as a whole, and such a displacement gives the observer's eyes an apparent beat pattern (moire) that is a gradation pattern having a larger pitch. This beam pattern (moire) has dependency such that a smaller displacement gives the beat pattern having a larger pitch, and a larger displacement conversely gives the beat pattern having a smaller pitch, and these displacement and pitch do not have individually settable values. Although the beat pattern apparently moves with the movement of the viewer's viewpoint, the moving speed also depends on the pitch of the beat pattern. This technique has such a constraint condition, and has a certain limit in versatility. In JP 2000-172203 A, strip-shaped two types of images are arranged alternately, and the pattern operator displays any one of the images depending on the viewing angle. This pattern generator is not configured to flow the image with the viewpoint movement.

SUMMARY OF THE INVENTION

In view of the above, the present invention aims to provide a pattern changing sheet, and a walking guidance system and a moving speed reduction device including such a pattern changing sheet that are capable of individually setting a gradation pattern corresponding to the pitch of optical elements and a display pattern displayed depending on the viewing angle, and of setting the moving speed of the display pattern at any scale factor of the moving speed of the head, i.e., of the viewpoint.

A pattern changing sheet according to the present invention has a display pattern as a gradation pattern to be observed from a viewpoint of a viewer, the display pattern progressing at a predetermined speed scale-factor of movement of the viewpoint. The pattern changing sheet includes: an optical element layer including optical elements at least in number corresponding to one wavelength of the pattern changing sheet, the optical elements being disposed with a first pitch in a direction orthogonal to the optical axis of the optical elements, each optical element having a light-transmitting part in a plane having a direction of disposing the optical elements and the direction or the optical axis, the light-transmitting part enabling the viewer to view inside of the optical element layer from a plurality of directions intersecting with the optical-axis direction; and a pattern layer disposed on a rear face of the light-transmitting part of the disposed optical elements to be opposed to the optical elements, the pattern layer having a gradation pattern having pixels assigned at positions on the rear face of the light-transmitting part so as to allow the viewer to view the pixels in the plurality of directions from the viewpoint to the optical elements. The display pattern of the one wavelength is expressed based on the pixels in each optical element, each pixel being assigned to a corresponding direction of the plurality of directions. The number of the pixels in the gradation pattern is set at a predetermined number so that, as the viewpoint moves while sequentially changing into an adjacent direction of the plurality of directions, the display pattern at the predetermined speed scale progresses repeatedly the predetermined number of times so as to progress by the one wavelength.

According to the present invention, when a viewer observes the optical element layer from a viewpoint, the viewer observes a pixel located at the observing angle via the light-transmitting part of each optical element, so that these pixels connect in the view in the disposing direction of the optical elements to be expressed as the display pattern. As the viewpoint moves, the display pattern of one wavelength sequentially progresses at the predetermined speed scale-factor in the disposing direction, and this induces vection. In this configuration, the first pitch and the wavelength of the display pattern have no dependency and can be individually designed. The wavelength of the display pattern and the speed scale-factor relative to the moving speed of the viewpoint also have no dependency, and can be individually designed. The present invention therefore creates and provides a pattern changing sheet having a high degree of freedom and depending on the intended use. The number of the gradation pattern formed in the pattern layer is not limited to the number corresponding to the display pattern of one wavelength, and the display pattern corresponding to a plurality of wavelengths may be formed in the disposing direction.

The gradation pattern satisfies the condition expressed by Expression 1.

[Mathematical 1]

$$n = \left\lfloor \frac{W}{L_0^*} \right\rfloor,$$

$$m = \left\lfloor \frac{\Delta W}{L_0^*} \right\rfloor,$$

$$j = \left\lfloor \frac{2\gamma\rho H}{DL_0^*}\tan\frac{\alpha}{2} \right\rfloor$$

(Expression 1)

In Expression 1,
dW<W/2, j<n/2;
$\lfloor \ \rfloor$ denotes floor functions;
design values n, m, and j are integers, and j<n/2, m<n;
W denotes one wavelength of the display pattern;

ΔW denotes the length of a bright part of the gradation pattern;

equivalent bus-line pitch $L_0^* = (1+h/H) \cdot L_0$, and $L_0$ denotes the first pitch;

H denotes a distance from the optical elements to the viewpoint;

h denotes the thickness of the optical elements;

D denotes the resolution;

γ denotes the speed scale-factor;

ρ denotes the density of bus lines; and

α denotes an expected angle.

This configuration allows individual designing the wavelength, the length of the pattern, and the speed scale-factor Expression 1. Since the virtual bus-line pitch and the bus-line pitch are commutative, designing based on any one of them leads to an equivalent result (substantially the same).

The present invention creates and provides a pattern changing sheet having a high degree of freedom and depending on the intended use. This pattern changing sheet is effectively used for training of gait, for example.

BRIEF DESCRIPTION OF THE DRAWINGS

FIG. 2 shows a parallax barrier having different wavelengths.

FIG. 3 describes a phase difference of the parallax barrier.

FIGS. 4A to 4D show cross-sections of two types of lenticular lenses having different bus-line pitches. FIGS. 4A and 4B are vertical cross-sectional views orthogonal to the bus line, and FIGS. 4C and 4D are vertical cross-sectional views in parallel with the bus line and along the optical axis.

FIG. 33 is a graph showing a change of the head position in the front/rear direction of (D, S)=(25, 45) in Experiment 4.

DETAILED DESCRIPTION OF THE EMBODIMENTS

Firstly the following describes the logic behind the designing of the pattern changing sheet 1 according to the present invention.

(Relationship Between Wavelength and Moving Speed)

Traveling waves with the wavelength L at the speed v need time T until the phase of the traveling waves shift by 2π at the observation point fixed in the world coordinate system, and so have the relationship of Expression 1:

$$T = L/v \qquad (1).$$

Figure 1:
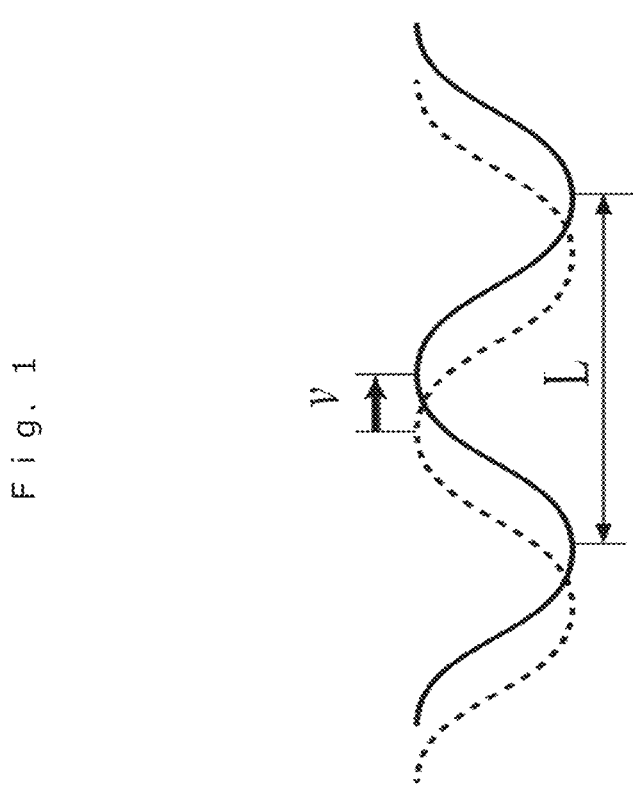
FIG. 1 describes the traveling of a wavelength L at the speed v.

See FIG. 1. The observation point observes the vibrations of the time period T, i.e., having the number of vibrations f=1/T=v/L. This shows that the number of vibrations, which is the number of nodes and antinodes of a visual stimulus that pass through the observation point, is inversely proportional to the wavelength L when the apparent speed v of the visual stimulus is constant.

(Analysis on Optical Conversion Element to Design Interference Fringes)

Examples of the optical elements used for the present invention include a parallax barrier, a lenticular lens and a fly eye lens. The following summarizes features of the optical elements that are necessary to design the moving speed of interference fringes that are observed with the observer's movement.

FIG. 2 shows a parallax barrier PB having different wavelengths as one example. This parallax barrier PB is made up of a barrier 200 and a base 300 that are opposed to each other. The barrier 200 has light-transmitting parts 200a and light-blocking parts 200b with the period of $L_1$. The barrier 300 has a printed face having bright parts 300a and dark parts 300b with the period of $L_2$.

For explanation's sake, let that $L_1 \approx L_2$, $L_1 < L_2$. Assuming that this parallax barrier PB includes these barrier and base overlaid with the distance d=0 therebetween as shown in FIG. 3, interference waves occur. As shown in FIG. 3, these interference waves have the occurrence phase that depends on the distance δ in the phase direction of the overlaying. Let that the barrier 200 on the $L_1$ side is fixed to the space, and the base 300 on the $L_2$ side is at the distance δ from $L_1$. Representing of this distance δ with the phase difference from the wavelength of $L_1$ gives the phase difference of $d\theta = 2\pi\delta/L_1$. Then, the spatial brightness distribution of the interference waves circles around in the range of $0 \leq \theta \leq 2\pi$. This shows that the moving distance on the $L_2$ side required for circling-around of the spatial brightness distribution of the interference waves is $L_1$. Some optical elements greatly change in the distance δ required for circling-around of the spatial brightness distribution of interference waves due to the principle of "optical lever" as described later, and the design of these optical elements requires careful attention.

That is the description on the interference waves observed from two waves having different spatial periods, and this description is applicable to understand a lenticular (cylindrical) lens. A lenticular lens has a cylindrical face, and the long-axis direction and the optical center of the cylindrical face is called a "bus line". The spatial period of these bus lines is called a lens pitch, and the lenticular lens has a function similar to the parallax barrier PB configured to have the spatial periodicity on the side to sample the printed face on the base 300 in FIG. 2.

The lenticular lens is different from the parallax barrier PB in that the moving distance of the viewpoint, which generates a phase difference dθ between $L_1$ side of the lens and $L_2$ side of the printed face of the base 300 as in FIG. 3, depends on the ratio of the spatial period of bus lines to the curvature r of the lenses.

FIG. 4 shows cross sections of two types of lenticular lenses, including flip lenses 11 each having the curvature r that are disposed at the bus-line pitch ≈2r, and 3D lenses 12 each having the same curvature r that are disposed at the bus-line pitch<<2r. The flip lens 11 is used to obtain the effect of switching (flipping and changing) of patterns, and the 3D lens 12 is used to obtain the binocular stereopsis effect.

To achieve an accurate apparent moving speed or a visual stimulus, the curvature of each lens has to be examined relative to the bus-line pitch of the lenses. To this end, an expected angle α is defined as shown in FIG. 4 for generalization, where the expected angle α represents the unit printing pitch. The expected angles in FIG. 4 are $\alpha_{flip}$ and $\alpha_{3D}$, where $\alpha_{flip} > \alpha_{3D}$. This magnitude relationship represents the magnitude relationship of the moving distance l required to observe one period of printing pitch at the same visual distance, and $l_{flip} > l_{3D}$ holds.

In many cases, the printing pitch is divided into N pieces of finite intervals for spatial multiplexing of the pattern to be stored. When the Flip lens and the 3D lens have the same division number N, the unit observation angle required for scanning of the divided unit intervals satisfies the relationship of $\alpha_{flip}/N > \alpha_{3D}/N$. This means that the 3D lens 12 expresses the pattern in different intervals with a smaller angular change than that of the Flip lens 11.

(Modelization of Interference Fringes (Interference Expression))

Figures 5A, 5B:
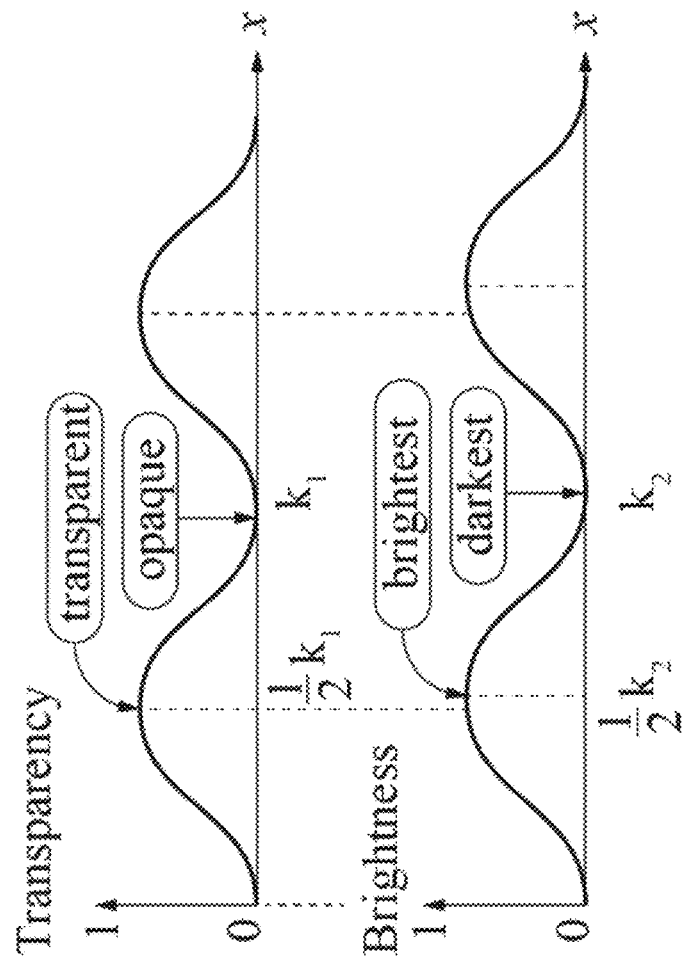
FIG. 5A shows the spatial distribution of transparency of an optical element.
FIG. 5B shows the spatial distribution of brightness immediately below the optical element.

Referring to FIG. 5, the following derives a model of interference fringes that occur between an optical element and a print pattern disposed immediately below the optical element. Let that selectively expressed bus lines have the spatial pitch of $k_1$ and the print pattern disposed immediately below the optical element has the spatial pitch of $k_2$. The following analytically derives the spatial frequency of the interference fringes. To this end, phenomena selectively expressed with the optical element are simplified, and are represented by the periodic function of Expression 2 as the spatial distribution of the transparency (FIG. 5A).

[Mathematical 2]

$$f(x) = \frac{1}{2} - \frac{1}{2}\cos\frac{2\pi}{k_1}x \quad \text{(Expression 2)}$$

Similarly the print pattern immediately below the optical element is represented by simplified Expression (3) as the gradation grating represented with a trigonometric function (FIG. 5B).

[Mathematical 3]

$$g(x) = \frac{1}{2} - \frac{1}{2}\cos\frac{2\pi}{k_2}x \quad \text{(Expression 3)}$$

Since the optical element selectively expresses the brightness and darkness of the print pattern, the product of f(x) and g(x) is calculated as in Expression 4.

[Mathematical 4]

$$f(x) \cdot g(x) = \left(\frac{1}{2} - \frac{1}{2}\cos\frac{2\pi}{k_1}x\right) \cdot \left(\frac{1}{2} - \frac{1}{2}\cos\frac{2\pi}{k_2}x\right) = \frac{1}{4}\left\{\begin{array}{c} 1 \\ -\left(\cos\frac{2\pi}{k_1}x + \cos\frac{2\pi}{k_2}x\right) \\ +\cos\frac{2\pi}{k_1}x \cdot \cos\frac{2\pi}{k_2}x \end{array}\right\} \quad \text{(Expression 4)}$$

In Expression 4, ¼ in the first term is a constant term, which is ignorable because it does not contribute to the spatial variation in brightness of the interference fringes.

The second term and the third term can be transformed addition theorem as in Expression 5.

[Mathematical 5]

$$(\text{Second term third term}) = \cos\frac{2\pi}{k_1}x + \cos\frac{2\pi}{k_2}x = \\ 2\cos 2\pi x\left(\frac{k_1+k_2}{2k_1k_2}\right)\cdot\cos 2\pi x\left(\frac{-k_1+k_2}{2k_1k_2}\right)$$ (Expression 5)

Interference fringes can be dealt with as the product of two different frequencies, and have a low-frequency component of $2k_1k_2/(k_2-k_1)$ and a high frequency component of $2k_1k_2/(k_1+k_2)$. Between them, the designing target for a visual stimulus is the low-frequency component. The above description holds based on the assumption of $k_1 \approx nk_2$ where n denotes an integer.

(Introduction of Visual Distance into Interference Expression)

To generate interference waves based on the bus-line pitch of the optical elements and the immediately below printed pitch, the visual distance affects the angular velocity of the spatial brightness phase of the interference waves in accordance with the observer's moving speed. To design the interference waves (interference fringes), the visual distance therefore has to be handled as a condition of constraint to design the print pattern.

As stated above, the relative distance δ to generate the phase difference dθ between the optical elements and the print pattern clearly depends on the distance d between the optical elements and the printed pattern (see FIG. 3), and the relative distance δ also depends on the visual distance from the $L_1$ face. Then, the following describes a variation of the phase difference between the bus-line pitch and the print pitch that occurs with the movement of the viewpoint position by the same distance as the bus-line pitch $L_0$.

Figure 6:
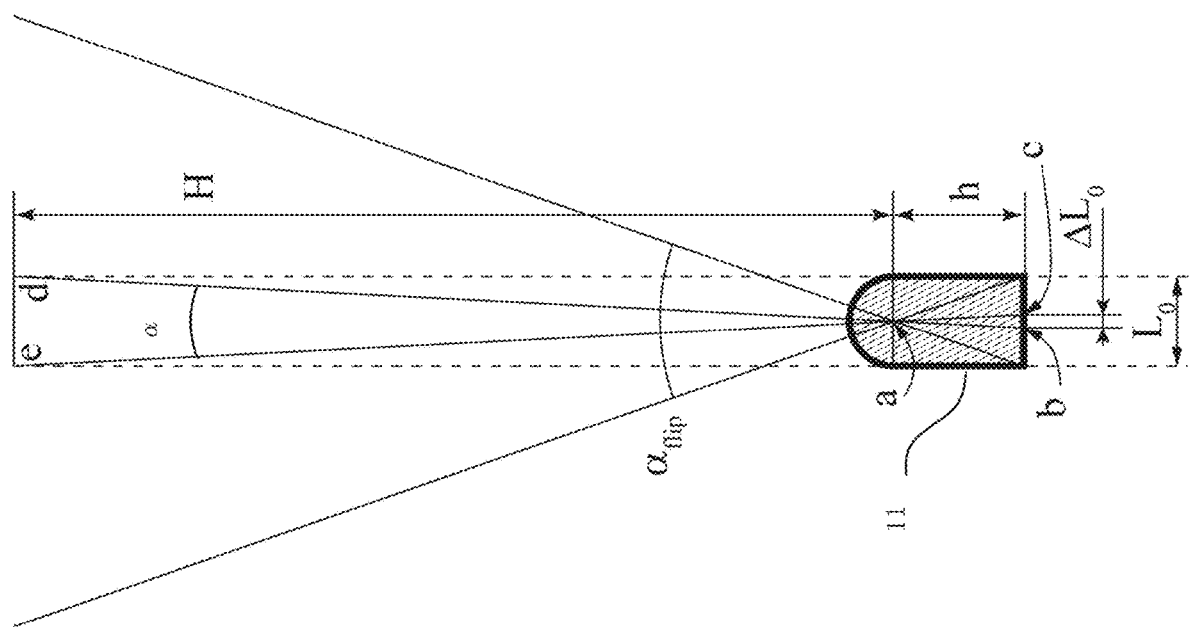
FIG. 6 shows the geometric relationship of the observing point at the visual distance H relative to the optical element.

Considering the usage of the present invention, the following assumes that the viewpoint position of the user is at the visual distance H from the optical elements having the bus-line pitch $L_0$. That is, assume that the user observes interference fringes from this position. FIG. 6 shows the Flip lens 11 again, which is shown in FIG. 4, and shows the lenticular (optical element 11) in this case. FIG. 6 additionally shows the observation position at the distance H from the optical element 11. In FIG. 6, the triangle abc and the triangle ade are similar, and so $\Delta L_0 = (h/H) L_0$ holds from this geometric constraint. To represent this with phase, assume that ∠bac is Δα. Then, a variation of the phase difference that occurs with the movement of the viewpoint position by the same distance as the bus-line pitch $L_0$ will be $\Delta\alpha/\alpha_{flip}$, and this is equal to $\Delta L_0/L_0$. This means that Δα can be obtained as in Expression 6.

[Mathematical 6]

$$\frac{\Delta\alpha}{\alpha_{flip}} = \frac{\Delta L_0}{L_0} = \frac{h}{H},$$ (Expression 6)

Transformation gives Δα as in $\Delta\alpha = \frac{h}{H}\alpha_{flip}$

When h=H, this corresponds to the description that the bus-line pitch $k_1$ and the print pitch $k_2$ can be dealt with as $k_1 \approx k_2$ as stated above. When h<<H, which is close to the usage of the present invention, the observer observes as if it were $k_1 \ll k_2$. This shows that the movement of the viewpoint corresponding to the bus-line pitch $L_0$ gives only a very small variation of the phase difference between the bus-line pitch and the print pitch.

In other words, the print pattern prepared with the design value of $k_1 \approx k_2$ has a very small phase variation of the brightness spatial distribution of interference fringes with the movement of the observing point. That is, this means that the moving speed of the visual stimulus will be observed at a very slow speed relative to the moving speed of the observing point.

The above description leads to the following design guideline. Specifically when the observing point at the visual distance H moves by the distance of the bus-line pitch to, the print pitch needs to be about $(h/H) L_0$ so as to change the phase difference between the bus-line pitch and the print pitch by 2π. This means that when h<<H, which is close to the usage of the present invention, the print pitch will be a very small value.

(Bus-Line Pitch and Printing Resolution)

The print pattern needs to be and is, preferably printed at high resolution. To achieve the advantageous effects of the present invention, the print-pattern has to be designed while considering the resolution limit of the print pattern.

Conventionally a technique called "changing" has been used for print-pattern designing. This technique spatially divides an image into strips and places such strips of a plurality of images alternately for switching by an "interlace" scheme. This can be implemented by placing a finite number of these strips in the bus-line pitch $L_0$ immediately below the optical element 11.

As the observing point at the visual distance H moves by the distance equal to the bus-line pitch $L_0$ of the optical elements 11, the intersection of the line reaching this observing point via point a with the print pattern scans the print pattern, and the scanning distance is $\Delta L_0$ (see FIG. 6). As stated above, $\Delta L_0 = (h/H)L_0$, and the above description indicates that when the observing point at the visual distance H moves by the distance corresponding to the bus-line pitch $L_0$, the print pitch needs to be divided into the distance of $(h/H)L_0$ so as to chancre the phase difference between the bus-line pitch $L_0$ of the optical elements 11 and the print pattern by 2π.

The unit of resolution used for printing is Dot Per Inch (DPI). For the optical elements 11 having periodicity, including lenticular lenses, the density of the elements is represented by the number of bus lines per unit distance, and Line Per Inch (LPI), which represents the number of bus lines per inch, is used as the unit. Using these units, a print pattern in the distance $(h/H)L_0$ that is the divided interval of the print pitch is formulated in the form of a discretization model. When a print pattern with the bus-line density ρ [LPI] is prepared with a printer with resolution D [DPI], the possible number of dots ξ per unit bus-line pitch can be obtained by ξ=D/ρ. To express different patterns depending on the viewpoint position, the lower limit is ξ≥2. Since $\Delta L_0 = (h/H)L_0$, Expression 7 gives the number of dots Δξ per $\Delta L_0$.

[Mathematical 7]

$$\Delta\xi = \frac{D}{\rho}\cdot\frac{\Delta L_0}{L_0} = \frac{Dh}{\rho H}$$ (Expression 7)

When no constraint condition h is given, the expected angles $\alpha_{flip}$, $\alpha_{3D}$ can be replaced with h. Expression 8 gives $\Delta\xi$ and $L_0$. Moving distance of the viewpoint required to express a print pattern at the same distance as the bus-line pitch $L_0$ is $2H \tan \alpha/2$, where H denotes the visual distance H and $\alpha$ denotes the expected angle. That since $\Delta L = L0/2H \tan \alpha/2$ substituting of this into Expression 7 gives Expression 8.

[Mathematical 8]

$$\Delta\xi = \frac{D}{\rho} \frac{L_0}{2H\tan\frac{\alpha}{2}} \quad \text{(Expression 8)}$$

Typical values are as follows.

$$D = 1.2 \times 10^3 [DPI] \quad \text{(Expression 9)}$$
$$\rho = 1.5 \times 10^1 [LPI]$$
$$\alpha = 40[deg]$$
$$L_0 = \frac{1}{\rho}[mm] = \frac{1}{15[LPI]} \cdot 25.4[mm] = 1.7[mm]$$
$$H = 1.7 \times 10^3 [mm]$$

Substituting of these typical values gives $\xi=8.0\times10$. This indicates that 80 dots can be placed in the bus-line pitch.

$\Delta\xi=1.1\times10-1<1$ holds, and this indicates that the number of dots placed in the scanning range $\Delta L$ on the print pattern during the movement of the viewpoint by the bus-line pitch $L_0$ falls below 1. This means that the viewer at the visual distance H is required to move the distance larger than distance $L_0$ to view one period of the minimum spatial pattern formed on the print pattern. In other words, the viewer moving by the distance $L_0$ will fail to observe the movement of interference fringes.

The upper-limit value of the spatial resolution of the print pattern therefore will affect the feasibility of the present invention. According to the sampling theorem, the print pattern has to be designed using a sufficiently high print resolution ID and a sufficiently large bus-line pitch $L_0$ that satisfy $\Delta\xi>2$.

Next the following describes how to implement the required visual stimulus and how to print a print pattern, based on the assumption that the print pattern is discretized in the units of printing dots.

(Lower-Limit Value of Spatial Pitch of Interference Fringes)

To express a print pattern immediately below the optical elements 11, assume that the optical elements 11 have the structure to sample a continuous print pattern in a discretized manner. Let that the sampling is performed with the bus-line pitch $L_0$, then the sampling spatial frequency will be $1/L_0$. Considering the Nyquist frequency, the reproducible upper-limit value of the spatial frequency component is $\frac{1}{2}L_0$. That is, the optical elements 11 do not express a spatial frequency component of the interference fringes higher than $\frac{1}{2}L_0$. This shows that the lower-limit value of the spatial pitch expressed by the optical elements is $2L_0$.

(Equivalent Bus-Line Pitch)

Figure 7:
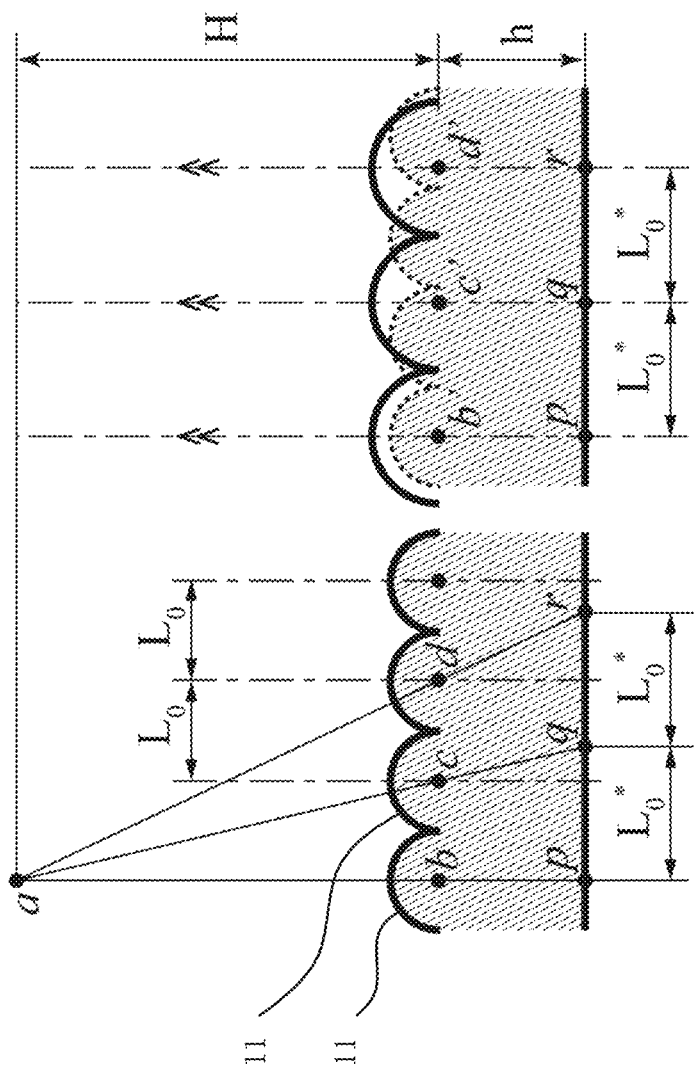
FIG. 7 explains the trajectory of light beams reaching the observing point and an equivalent bus-line pitch that makes the light beams reaching the viewing point parallel to each other.

A group of light beams to be considered to design a print pattern is equivalent to a group of light beams in various directions shown in FIG. 7 on a plane including the optical-axis direction and the pitch direction that start from the observing point a, pass through the corresponding optical elements 11, and reach the print pattern on the rear face. The formed group of light beams passing through the optical centers of these optical elements 11 (lines abp, acq, and adr) are not in parallel and intersect at the observing point a. Strictly speaking, the observed pattern during the movement of the viewpoint position (observing point a) needs tracking of the group of light beams as shown on the left of FIG. 7.

The designing of a print pattern for the bus-line pitch $L_0$ can be simplified by setting the group of light beams that are in parallel as shown on the right of FIG. 7. To this end, the bus-line pitch $L_0$, which is an optical characteristic of the optical elements 11, is corrected, and an equivalent bus-line pitch $L^*_0$ is defined to make the light beams passing through the optical center in parallel as shown on the right of FIG. 7. In the present invention, the equivalent bus-line pitch $L^*_0$ and the bus-line pitch $L_0$ are commutative. As shown FIG. 7 on the left, the group of light beams start from the observing point a, passes through the optical center points b, c, and d of the optical elements 11 and reaches points p, q, and r on the print pattern. The equivalent bus-line pitch $L^*_0$ is the distance between points p, q, and r. Since $|bc|=|cd|$, $|pq|=|qr|$. Triangles $\Delta abc \propto \Delta apq$ are similar due to the geometric constraint, and so the equivalent bus-line pitch. $L^*_0$ can be represented by Expression 10 since H>0.

[Mathematical 9]

$$|bc|:|pq| = H : H + h = L_0 : L_0^* \quad \text{(Expression 10)}$$
$$L_0^* = \left(1 + \frac{h}{H}\right)L_0$$

When the observing point is at infinite distance, $H \to \infty$ holds, and then Expression 10 gives $L^*_0 \to L_0$. Points b, c, and d are light-transmitting parts of the present invention.

(Discretization Print-Pattern Model)

Figure 8:
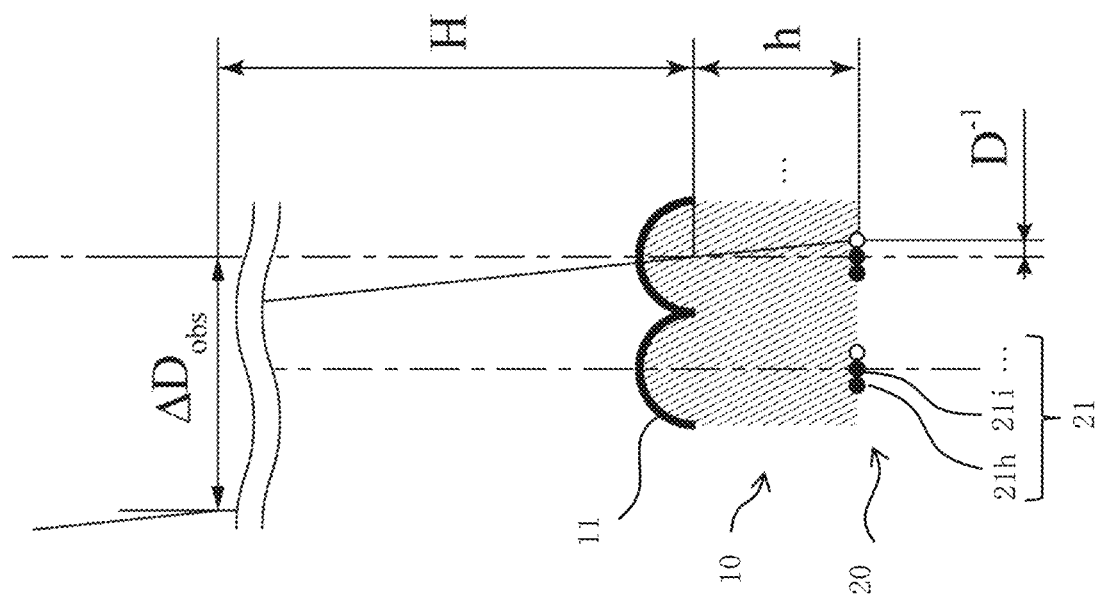
FIG. 8 explains the moving distance of the viewpoint position required to express adjacent dots.

Based on the above description, the following derives a design model of a print pattern based on the assumption that the spatial resolution of the print pattern has the upper-limit value. Based on the above description, the moving distance $\Delta D_{obs}$ at the visual distance (viewpoint distance) H, which is required to express dots $21h$, $21i$, ... as the pixels that are formed side by side on a sheet-like pattern layer 20 opposed to the lower face of the optical elements 11 making up an optical element layer 10 as shown in FIG. 8, corresponds to division of the moving distance $2H \tan (\alpha/2)$ to express the print pattern (gradation pattern) 21 corresponding to the bus-line pitch $L_0$ by the number of the dots $21h$, $21i$, ... stored in the bus-line pitch $L_0$. That is, the moving distance $\Delta D_{obs}$ can be represented by Expression 11.

[Mathematical 10]

$$\Delta D_{obs} = 2H\tan\frac{\alpha}{2} \cdot \left(\frac{D}{\rho}\right)^{-1} \quad \text{(Expression 11)}$$

Expression 11 can be represented as $2H \tan \alpha/2 \cdot (D/\rho)^{-1} = H/hD$, and this gives $h=\frac{1}{2}\rho \tan \alpha/2$.

Substituting of typical values (see Expression 9) into the above expressions gives the approximate value of $\Delta D_{obs}=1.5\times10$ [mm]>>$L_0$=1.7 [mm]. This shows that, in order to express adjacent dots $21h$, $21i$ . . . at the visual distance H, the moving distance (and the speed scale-factor)

required will be about ten times the bus-line pitch of the optical elements 11. That is, the constraint condition due to the upper-limit value of the print resolution corresponds to $L_1 \ll L_2$ in FIG. 2 and FIG. 3 or $k_1 \ll k_2$ in FIG. 5.

The print pattern 21 can be designed by defining a pattern to be expressed by the optical elements 11 when the viewpoint position moves by the distance $\Delta D_{obs}$, where the distance $\Delta D_{obs}$ is the distance required to express the adjacent dots 21$h$, 21$i$ . . . .

Figure 9:
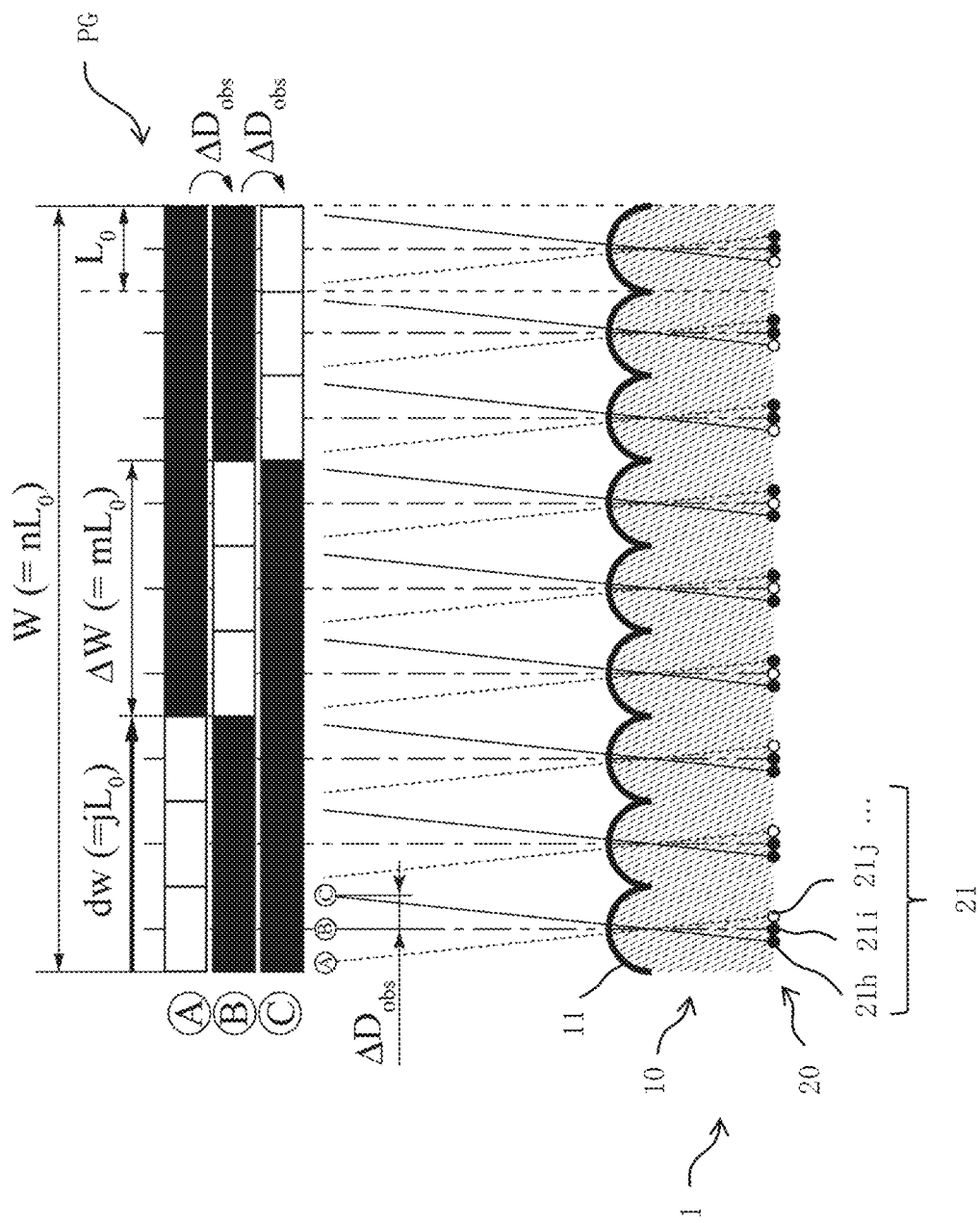
FIG. 9 shows a global pattern (bright/dark ratio: 1:2) expressed with the light and dark alignment of the adjacent dots. The upper half of FIG. 9 shows a pattern displayed on the optical element, and the lower half of FIG. 9 is a cross-sectional view of the bus-line pitch of the optical elements.

FIG. 9 shows an example of the pattern expressed by the optical elements 11 with the movement of the observing point at the visual distance H by the distance $\Delta D_{obs}$. For easy understanding, FIG. 9 shows an example of the pattern of one wavelength, and shows all of the light beams in a group converged at the observing point that are parallel light beams. These light beams can be obtained by correction by the method described above (equivalent bus-line pitch), which will be described later in details.

Encircled A, B, and C at the upper half of FIG. 9 represent a global pattern (display pattern PG) expressed on the optical elements 11. This display pattern PG is divided with the bus-line pitch $L_0$ in the horizontal direction, which is the same distance as the bus-line pitch $L_0$ of the plurality of optical elements 11 making up the optical element layer 10 of the pattern changing sheet 1 shown in the lower half of FIG. 9. In this example, bright and dark parts in one wavelength W is observed as a global pattern, which is common to the encircled A, B, and C at the upper half of FIG. 9. The differences among the encircled A, B and C correspond to differences in optical path reaching to the observing point.

The encircled A, B and C at the upper half of FIG. 9 represent the optical paths for dots 21$h$, 21$i$, 21$j$ . . . corresponding to the optical paths of the encircled A, B and C at the lower half of FIG. 9. The patterned layer 20 has the print pattern and the print pattern 21 includes the combination of dots 21$h$, 21$i$, 21$j$ . . . . The print pattern 21 is formed at the patterned layer 20 opposed to the optical elements 11. The dots 21$h$, 21$i$, 21$j$ . . . are pixels corresponding to (assigned at) the positions in parallel with the pitch direction. In another embodiment, the patterned layer 20 may be disposed on the rear face of the optical elements 11. Preferably the print pattern 21 is at a substantially focal distance of the optical elements 11.

For explanatory convenience, the dots 21$h$, 21$i$, 21$j$ . . . in this embodiment are indicated as white and black small circles (representing bright parts and dark parts). As described above (equivalent bus-line pitch), intersections of the visual distance H and the optical paths A, B, and C have the intervals of $\Delta D_{obs}$. In other words, FIG. 9 shows that the optical paths reaching the observing point change as in A→B→C for each movement of the observing point by the distance $\Delta D_{obs}$. As shown in the lower half of FIG. 9, the print pattern 21 has the alignment of "black circle, black circle, white circle" in the optical element 11 at the left end among the nine optical elements 11, for example, when the observing point moves by the distance twice the distance $\Delta D_{obs}$. This gives the view changing like "white→black→black" to the observer. The print pattern 21 has the same alignment of "black circle, black circle, white circle" in the three optical elements 11 close to the left end, and this gives the view changing like "white→black→black" to the observer during movement.

The print pattern 21 has the same alignment of "black circle, white circle, black circle" in the three optical elements 11 at the center, and this gives the view changing like "black→white→black" to the observer during movement.

The print pattern 21 has the same alignment of "white circle, black circle, black circle" in the three optical elements 11 close to the right end, and this gives the view changing like "black→black→white" to the observer during movement. This example has the alignment of the print pattern 21 corresponding to the optical elements 11 in the units of three adjacent dots so as to correspond to the equivalent bus-line pitch, and the same (common) print pattern is aligned for the adjacent three optical elements 11 as shown in the lower half of FIG. 9. In this example, each print pattern 21 is made up of the number of dots (pixels) of 3×9.

The upper half of FIG. 9 clarifies the relationship between the optical elements 11 and the print pattern 21 while focusing on these optical elements 11, and shows bright parts and dark parts of the expressed pattern in the absolute coordinate system. Note that this does not show the relative positional relationship viewed from the observing point.

Figure 10:
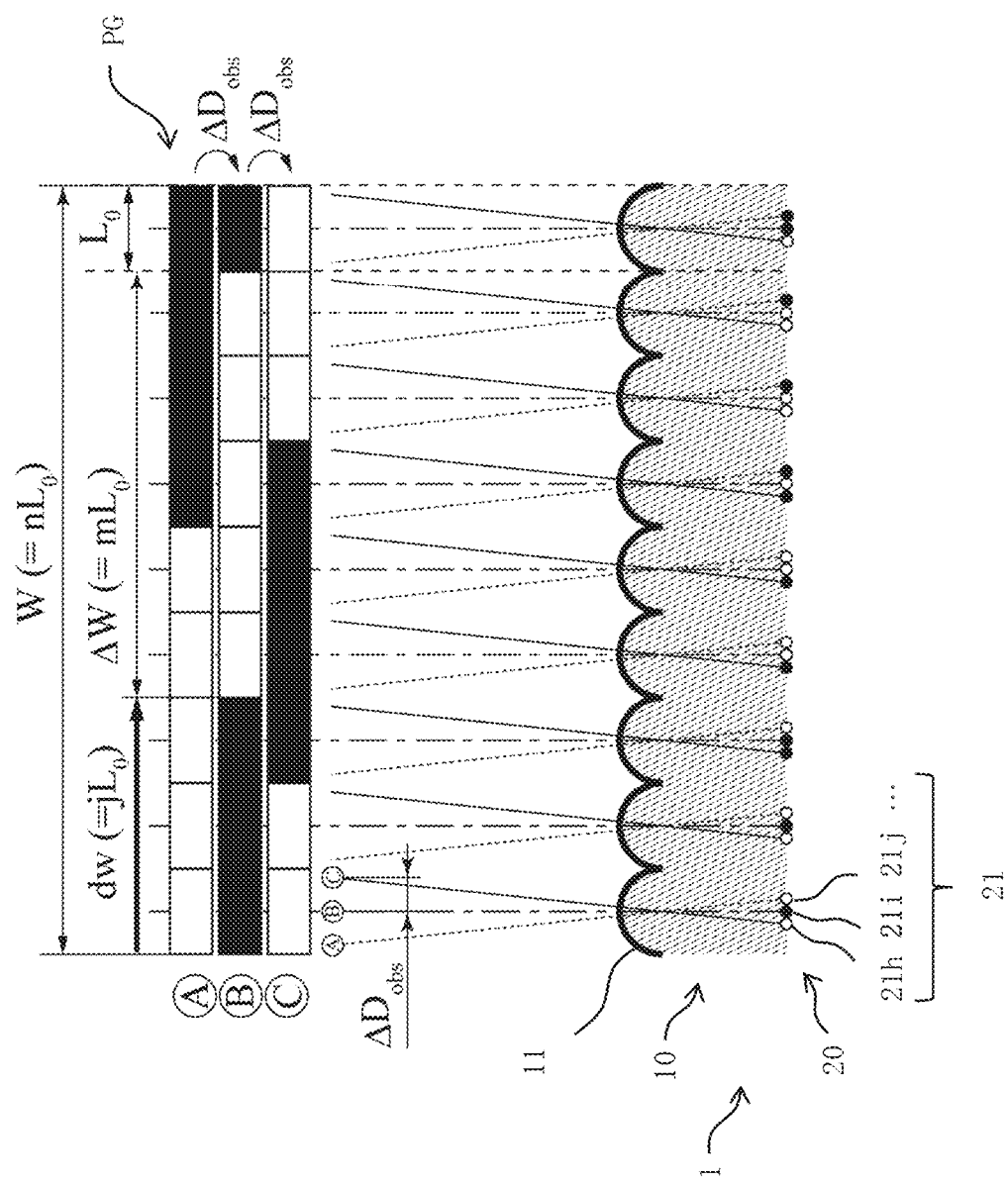
FIG. 10 shows a global pattern (bright/dark ratio: 5:4) expressed with the light and dark alignment of the adjacent dots. The upper half of FIG. 10 shows a pattern displayed on the optical element, and the lower half of FIG. 10 is a cross-sectional view of the bus-line pitch of the optical elements.

Next the following describes a design requirement so as not to make the flowing direction of a visual stimulus that a user sees ambiguity. Considering the brightness change in the axial direction orthogonal to the bus line of the expressed pattern as pulse-modulated square pulses, designing of the print pattern 21 is required to have a pulse-width ratio so as to satisfy $\Delta W/W \neq 1/2$, $0 < \Delta W < W$, where W denotes the wavelength and $\Delta W$ denotes the length of a bright part as shown in FIG. 9. FIG. 9 shows an implementation example of the bright/dark ratio of the pulse width that is 1:2, and FIG. 10 shows an implementation example of the bright/dark ratio of the pulse width that is 5:4. The configurations shown in FIG. 9 and FIG. 10 show one embodiment of a pattern changing sheet according to the present invention. The bright/dark ratio is not limited to this embodiment, which may be embodied variously. The pattern is not limited to white and black, which may be halftone, gradation, or colored. Examples of the pattern include bright and dark (gradation) pulses, stripes, and others.

The movement of a visual stimulus is observed in the direction smaller than a half period of the spatial period W of the visual stimulus, and so the maximum movement dw per reproducible unit-dot switching has the upper-limit value of $dw < W/2$. That is, the reproducible unit-dot switching frequency (repeating frequency) is at least three times. Both of the wavelength W and the bright-part length $\Delta W$ can be discretized with the bus-line pitch $L_0$, and $W = nL_0$, $\Delta W = mL_0$. This means that n and m have to be clarified as the design values, and these values are obtained by the following Expression 12 using a floor function.

[Mathematical 11]

$$\therefore n = \left\lfloor \frac{W}{L_0} \right\rfloor, m = \left\lfloor \frac{\Delta W}{L_0} \right\rfloor \quad \text{(Expression 12)}$$

The present invention is configured to allow the optical elements 11 to express the real-number multiple of the moving speed of the user's head in parallel. To this end, the moving distance dw of the display pattern PG expressed corresponding to the unit moving distance dx of the viewpoint is defined (FIG. 9 and FIG. 10). Since $dx/dt = v_{eye}$, the required speed $v_{reg}$ can be a real-number multiple of the head moving speed $v_{eye}$ as in Expression 13.

[Mathematical 12]

$$\frac{dw}{dt} = v_{req} = \gamma v_{eye}$$

$$\frac{dw}{dx} = \frac{dt}{dx} \cdot \frac{dw}{dt} = \frac{1}{v_{eye}} \cdot \gamma v_{eye} = \gamma$$

$$\therefore \frac{dw}{dx} = \gamma$$

(Expression 13)

The unit moving distance dx is discretized into the unit distance $\Delta D_{obs}$ for switching of the dots for expression, and so dw can be represented as in the following Expression 14 based on Expression 11.

[Mathematical 13]

$$dw = \gamma dx = \gamma \Delta D_{obs} = 2\gamma H \tan\frac{\alpha}{2} \cdot \left(\frac{D}{\rho}\right)^{-1}$$

(Expression 14)

Note here that dw has the upper-limit value of dw<W/2. As shown in FIG. 9, dw is discretized with the bus-line pitch $L_0$, and so j satisfying $dw=jL_0$ can be obtained by the following Expression 15 using a floor function.

[Mathematical 14]

$$\therefore j = \left\lfloor \frac{dw}{L_0} \right\rfloor = \left\lfloor \frac{2\gamma\rho H}{DL_0}\tan\frac{\alpha}{2} \right\rfloor$$

(Expression 15)

The bus-line pitch $L_0$ used in Expressions 12 and 15 can be replaced with the above-stated equivalent bus-line pitch $L^*_0$ so as to compensate an error occurring because a group of light beams reaching to the observing point is considered as parallel light beams in FIG. 9 and FIG. 10. In Expressions 12 and 15, replacement with the equivalent bus-line pitch $L^*_0$ gives Expression 16.

[Mathematical 15]

$$\therefore n = \left\lfloor \frac{W}{L^*_0} \right\rfloor, m = \left\lfloor \frac{\Delta W}{L^*_0} \right\rfloor, j = \left\lfloor \frac{2\gamma\rho H}{DL^*_0}\tan\frac{\alpha}{2} \right\rfloor$$

(Expression 16)

j, m and n are integers, and j<n/2, m<n.

That is the details for the designing of the discretized print pattern 21 to implement the required speed scale-factor γ. In this way, individual setting of $L_0$ (equivalent $L^*_0$), W, ΔW, and γ enables designing of n, m, and j. In one example, a desired value can be set for the speed scale-factor γ. Let that γ=10, the wavelength V and ΔW to determine the bright/dark pattern can be individually set without constraint from γ=10. This leads to an advantage of having a high level of tolerance to implement the design depending on the intended use. FIG. 9 and FIG. 10 show the configuration of the movement of one period pitch (one wavelength) with three dots. In another embodiment, the movement of one period pitch (one wavelength) corresponds to four or more dots. A larger number of dots of one period moves the print pattern 21 more smoothly. The values of n, m, and j may be equivalently (i.e., substantially the same) designed by any one of Expression 16 and Expressions 12 and 15.

According to the above description, the speed scale-factor can be adjusted by adjusting the width between the adjacent dots or by adjusting beforehand the combination of bright and dark dots of the print pattern 21 making the display pattern so as to correspond to switching of the dots to express a display pattern progressing with the movement by the distance $\Delta D_{obs}$. Both of these adjustments may be made for the speed scale-factor.

Next the following describes one embodiment of the application of the pattern changing sheet as described above.

(Frozen Gait Due to Parkinson's Disease)

Parkinson' disease is one of the diseases currently designated as intractable in Japan. Main symptoms of this disease include "frozen gait". "Frozen gait" is one type of gait difficulty, such as the difficulty in taking an initial step of the gait or falling due to the weakness at knees. There are many views on the reason of this frozen gait, and the patients often experience the frozen gait at the initial step to start walking or to change the walking direction, at a narrow space, or when they notice an obstacle. Various rehabilitation methods for frozen gait are available, including a method of putting a mark on the floor with tape and encouraging the patient to step over the mark, or of encouraging the patient to step forward to a steady rhythm. The following description focuses on the difficulty in taking an initial step of the gait as one of the symptoms of the "frozen gait". Humans stabilize their posture based on the visual prompt during gate. Then the following considers visually-induced self-motion perception (hereinafter called vection) that every person experiences. When observing a visual pattern moving in a certain direction, the observer feels illusion like that they have moved in the opposite direction. Vection refers to such an illusory phenomenon and feeling. The following describes a method to give the visual stimulus in the environment to cause a body swaying and achieve the initial step of the gait by the viewer.

(Conventional Rehabilitation Technology)

The followings are examples of the currently conducted rehabilitation techniques.

"Technique 1" askes a patient to start a motion to step over the line (tape applied) on the floor.

In "Technique 2", a patient carries a laser to illuminate the floor with a laser beam, and is asked to start a motion to step over the laser beam.

"Technique 3" asks a patient to sway the body forward and backward to start a motion.

"Technique 4" asks a patient to start a motion while singing a song.

"Technique 5" asks a patient to start a motion by repeatedly talking to them like "go, go, go" or "turn, turn, turn".

Technique 1 has a feature of giving the patient a visual prompt that is the line on the floor for easy understanding of the place to step forward and for easy stepping-forward. This technique, however, requires drawing a line (applying tape) on the floor for every initial step, and so lacks the convenience. In contrast, Technique 2 gives a visual prompt anywhere because the patient carries a laser issuing a laser beam. This technique, however, has a concern of wobbling of the mark to be stepped over because this visual prompt as a laser beam also moves with the gait of the patient. Technique 3 asks the patient to sway the body firstly for easy starting of the gait without starting the gait from the stationary condition, and is not visually affected. Techniques 4 and 5 are for easy starting of the gait by keeping rhythm, and are not based on a visual prompt similarly to Technique 3.

According to "Study of Postural Response to Horizontal Swaying of Platform", Hirotoshi Fujiwara, Practical Otolaryngology, Vol. 77 (1984), No. 1 special pp 171 to 195 (https://www.jstage.jst.go.jp/article/jibirin1925/77/1special/

77_special_171/_pdf), a certain stimulus was given to a subject having a stationary posture while standing upright, and the postural response to the stimulus was observed for clear understanding of the relationship between the stimulus and the response during the upright-posture control. Specifically the postural response was observed when various stimuli, such as an optokinetic stimulus, a labyrinthine stimulus, a linear motion of a platform, inclination, and a vibration stimulus to the antigravity muscle, were given to the subject standing upright. To clarify the mechanism of controlling the upright posture, physiological stimuli that induce the postural response acting as a stimulus to keep the typical upright posture have to be selected. To this end, this study observed postural responses when a horizontal swaying motion was given to the platform. The study reported the followings.

(1) Body parts including the head, shoulders, hip, and knees moved in the substantially same phase with the platform moving at a small frequency (about 0.3 Hz), and an increase in the frequency of the platform motion led to remarkable differences in phase difference among these body parts. The phase difference increased in the order of knees, hip, shoulders, and head. The phase delay of the head was about 180° at 1 Hz and about 360° at 3 Hz.

(2) As the frequency of the platform motion increased, the amplitude of knees, hip, shoulders, and head decreased compared to the amplitude of the platform.

(3) The amplitude of the upper-body swaying was larger when the subject closed eyes than when they opened eyes with the slow motion of the platform like 0.3 Hz and 1 Hz. Such a difference was not found between closed eyes and open eyes with a quick motion like 3 Hz.

(4) At the frequency exceeding 1 Hz, the upper body and the lower body swayed with the hip as the supporting point for both of the opening eyes and the closed eyes.

(5) Visual input reduced the upper-body swaying at small frequencies (about 1 Hz or less).

Considering the above, visual input controls the body swaying well when the platform sways at small frequencies (about 1 Hz or less).

Next the following describes the reason of a visual stimulus affecting a body motion. Examples of visual stimulus affecting a body motion include vection, i.e., visually-induced self-motion perception. When a homogeneous motion stimulus is given to the wide visual field of a viewer, the viewer feels an illusion like their body has moved in the direct on opposite of the motion direction of the stimulus. This illusion is called vection. Vection often appears in our daily lives as well. For example, when one in a train sees another train on the other side start to move, the one can have the illusion that one's own train has started to move.

(Designing Method of Visual Stimulus)

The following provides a method of designing a visual stimulus that promotes the body swaying a subject and encourages a subject to take a step that is means of enlarging the optical flow of a visual stimulus obtained from body swaying. That is, the method derives an increasing scale-factor of the moving speed of a visual stimulus that enables a body-swaying period and a body-swaying amplitude to induce a stepping-forward motion and enables a visually-induced motor reflex at least under such a condition to induce a stepping-forward motion.

While conventional rehabilitation methods give a patient a visual stimulus fixed on the floor, no methods have been proposed to increase the moving speed of the visual stimulus based on the head motion, and so increase the body swaying. In principle, the effect of enhancing the body swaying can be expected from such a method, and so the method is effective to induce the stepping-forward motion.

(Principle and Mechanism of Visual Stimulus)

Figures 11A, 11B:
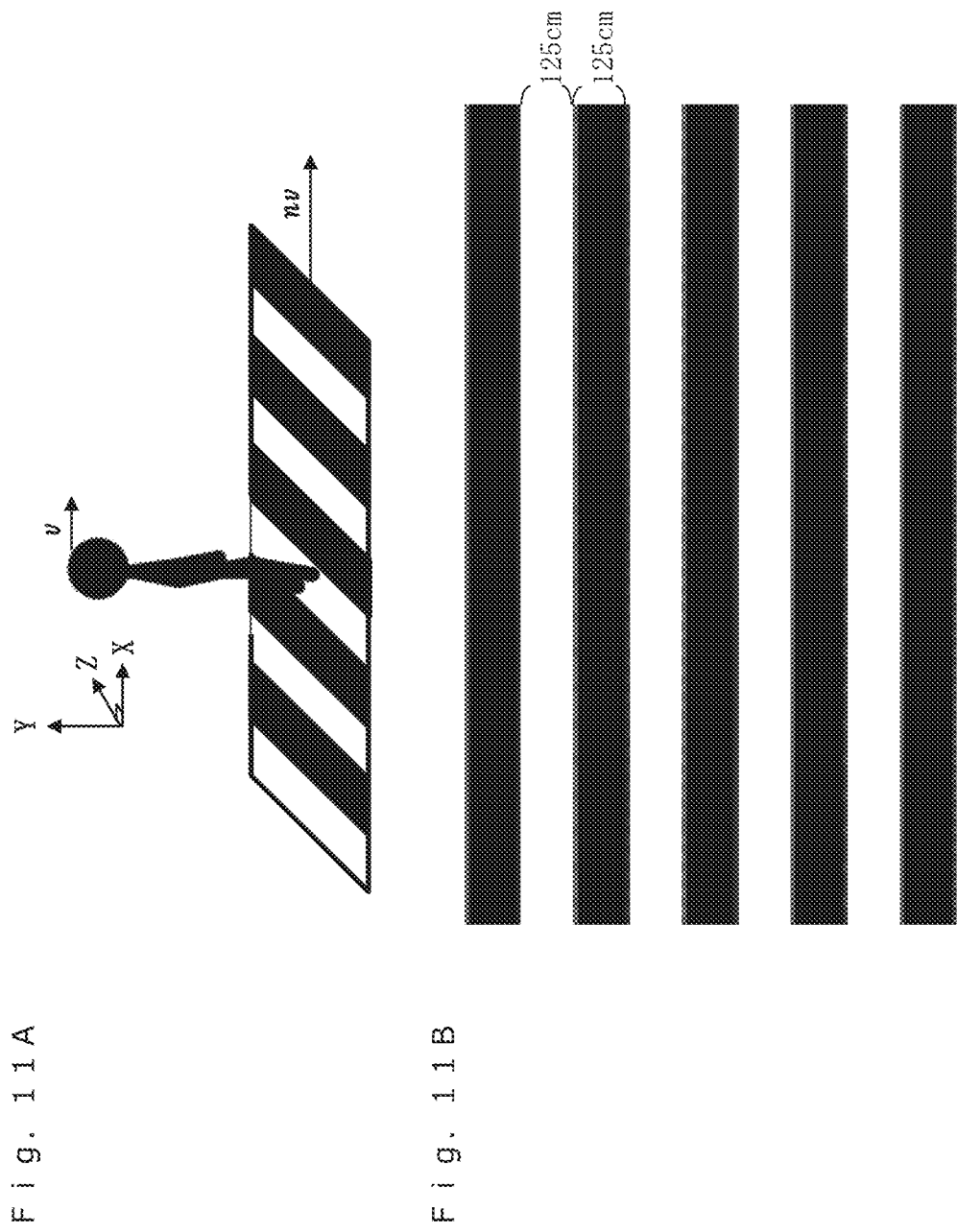
FIG. 11A shows an image of Experiment 1, and shows the relationship between the head speed and the visual stimulus.
FIG. 11B is a plan view of one example of the presented image.

The following describes a method for designing a visual stimulus that gives a user a visual stimulus at the speed n times the speed of the head motion in the head-motion direction, and specifies the procedure for experience. The conditions of a visual stimulus that moves the floor at the speed n times the head speed is defined as the scale-factor condition=n (see FIG. 11A), and a determination on the effectiveness is made based on whether the viewer is able to step forward or not. Note that n≥0. When the head motion is a translation motion at the speed v in the positive direction of x-axis in the world coordinate system, the visual stimulus is defined to have the speed nv in the positive direction of this axis.

(Experiments 1 to 4)

Firstly the following describes the effect of enhancing the body swaying when a visual stimulus is given to a subject in an upright state without swaying forward and backward in these verification experiments, a participant of the experiment wore a Head-Mounted-Display (hereinafter abbreviated as HMD) to observe an image simulated with a computer. To control the stimulus, the HMD used was HTC vise (resolution: 2060×1200, refresh rate: 90 Hz, viewing angle: about 110°, weight: 555 g). The HMD was equipped with an acceleration sensor and a gyroscope sensor to detect the display's motion, and was configured to be measurable of the moving speed f the head wearing the HMD in the front-and-rear directions. Instead of these sensors, the moving speed of the head may be calculated from an image taken by an external imaging unit, or may be detected with a magnetic three-dimensional position sensor.

(Experiment 1)

In Experiment 1, a participant was asked to stand upright while facing forward for 15 seconds. The participant was asked to stand in the Romberg's upright position to control their motion. The presented image corresponded to a display pattern PG used in the present invention. In this example, the display pattern was black/white stripes each having the width of 125 mm (see FIG. 11B). Instead of an actual pattern changing sheet 1 of the present invention, this experiment presented a floor image that moved at the speed proportional to the head speed in the HMD configured to show the same image as the pattern changing sheet 1.

In Experiment 1, the participant was asked to try three patterns, including closing eyes, scale-factor condition=0, and scale-factor condition=80. The number of the participants was tour, and they were healthy men in their 20s to 30s. The HMD was equipped with an image display unit that displays a presented image while moving the image at a speed multiplied by a predetermined scale-factor in accordance with the measured moving speed in the same direction as the head-moving direction.

Figure 12:
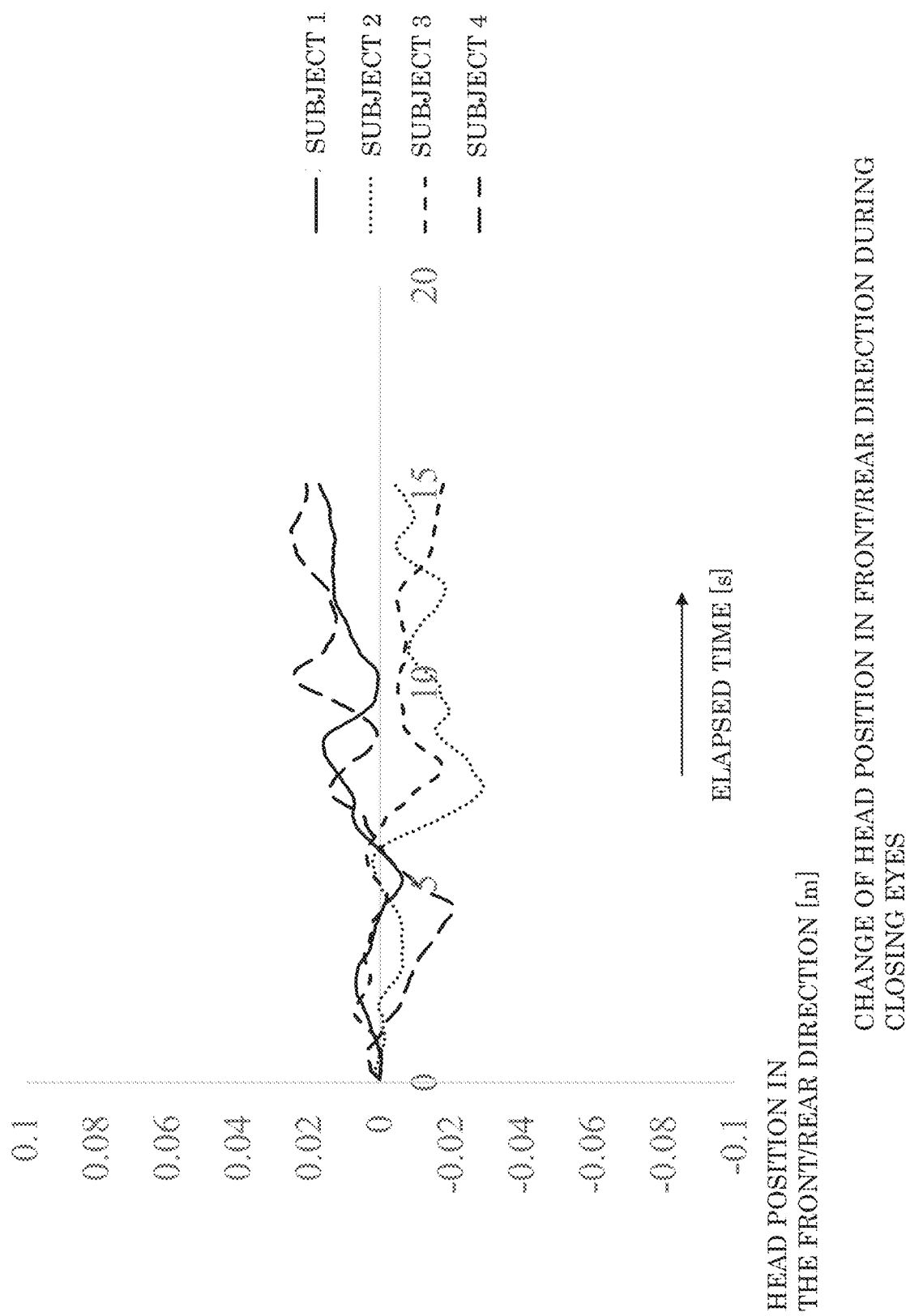
FIG. 12 is a graph showing a change of the head position in the front/rear direction during the closing eyes in Experiment 1.
Figure 13:
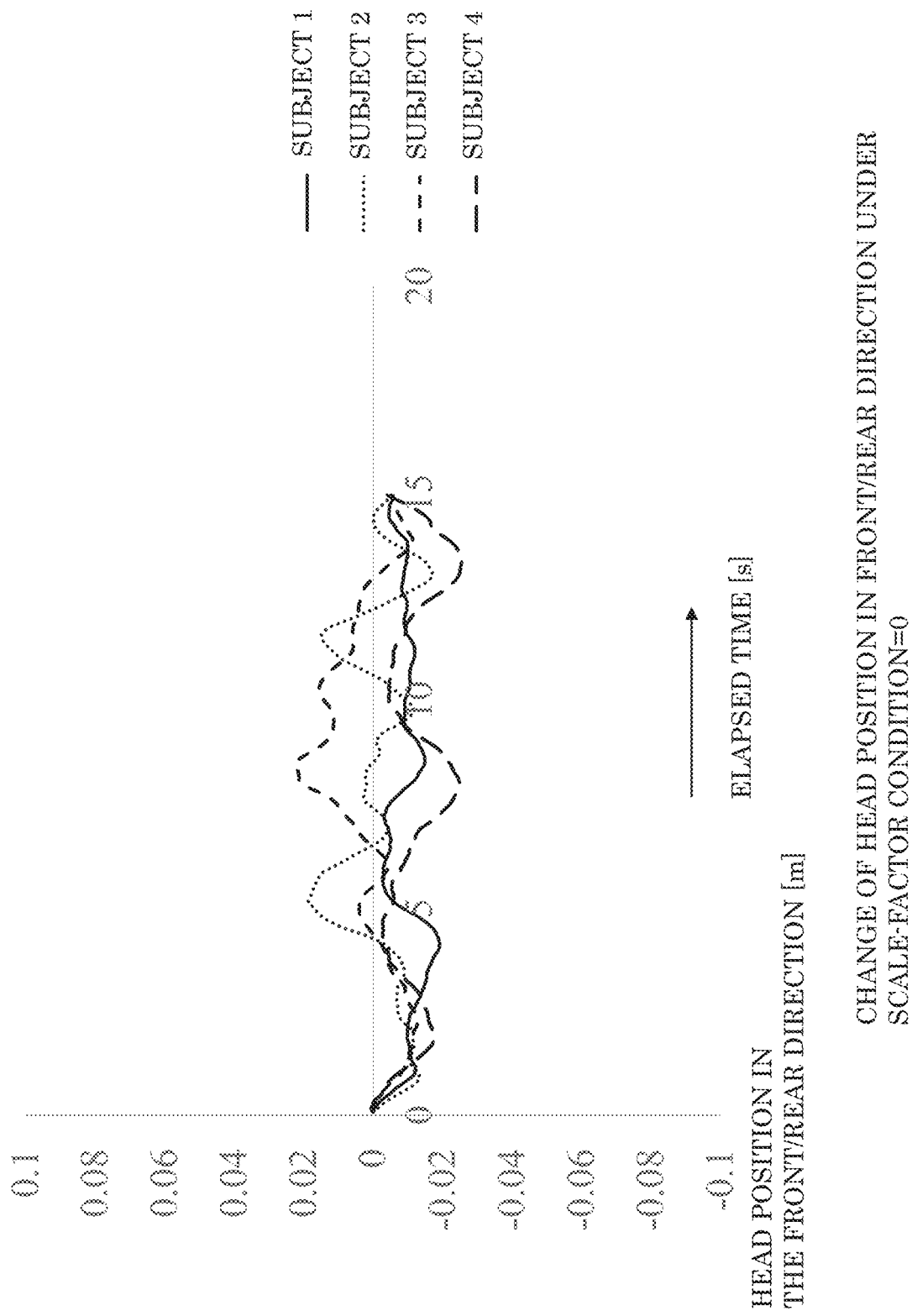
FIG. 13 is a graph showing a change of the head position in the front/rear direction under the scale-factor condition=0 in Experiment 1.
Figure 14:
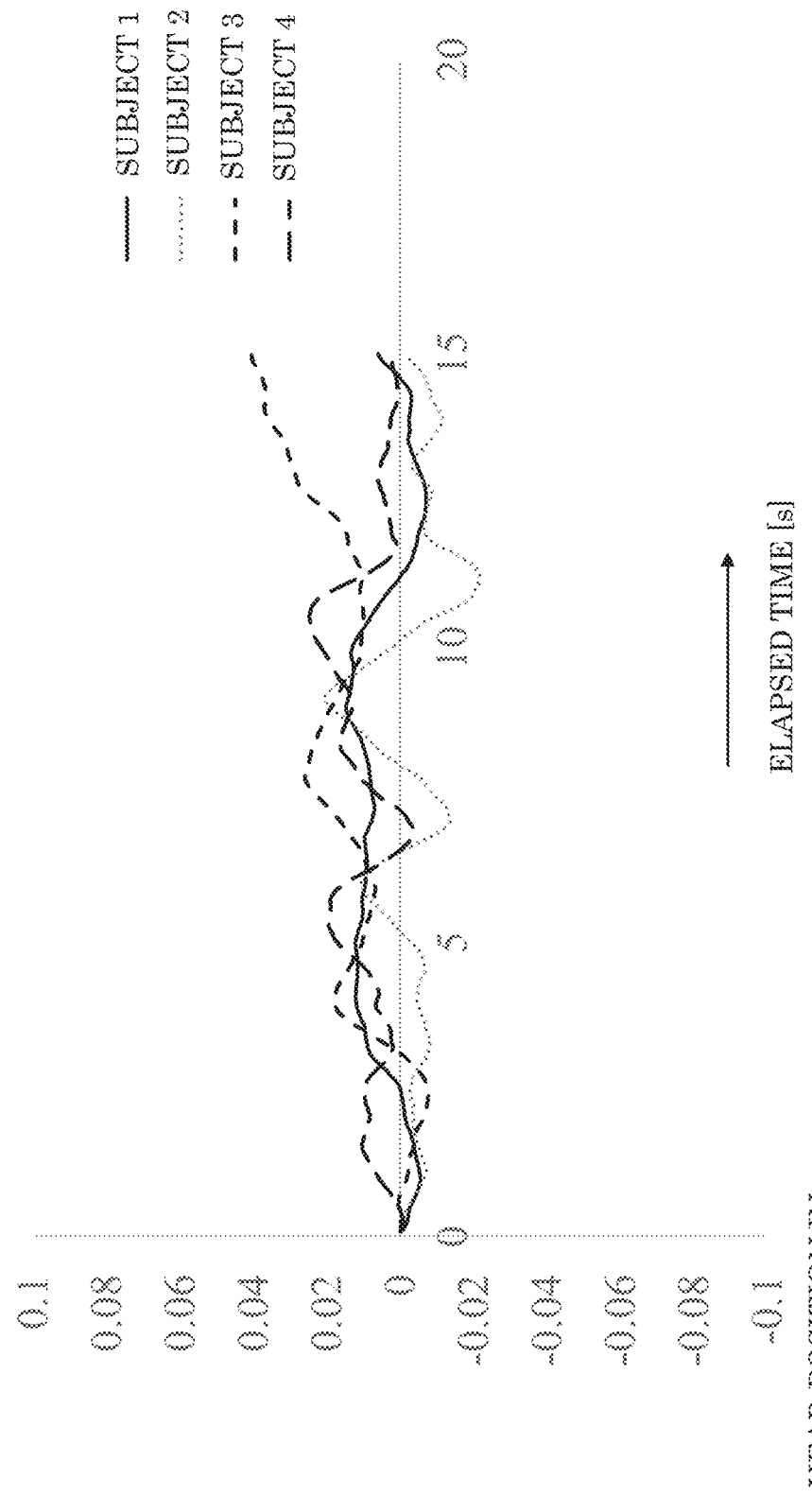
FIG. 14 is a graph showing a change of the head position in the front/rear direction under the scale-factor condition=80 in Experiment 1.

FIGS. 12, 13 and 14 show the result corresponding to the conditions to show the magnitude of the head motion. These drawings show the position of the head (vertical axis) in the front/rear direction (x direction in FIG. 11) versus the elapsed time (horizontal axis). The origin is the head position at the starting of the experiment, and positive and negative correspond to the front and the rear, respectively.

FIG. 12, FIG. 13, and FIG. 14 show that the head swaying was within 4 cm forward and backward in any condition. This is because, although Experiment 1 aimed to induce a body swaying from the head swaying of the person standing upright and so amplify the forward/backward swaying, the visual stimulus in this experiment was insufficient to induce the body swaying because the swaying width of the head swaying was small, and the motion of the floor pattern in the presented image accordingly was small. This shows that a swaying width to induce a body swaying has to be the head swaying or more of the person standing upright.

(Experiment 2)

Experiment 1 confirms that the swaying width of the head swaying of a person standing upright fails to induce the body swaying. Based on this, Experiment 2 asked a participant to start the experiment from the state of inclining the upper body relative to the upright position. This is to keep certain amplitude of the head swaying. This kept the swaying width of the head required to induce the body swaying, and this experiment verified whether the body swaying effective for the stepping-forward was obtained or not.

Figure 15:
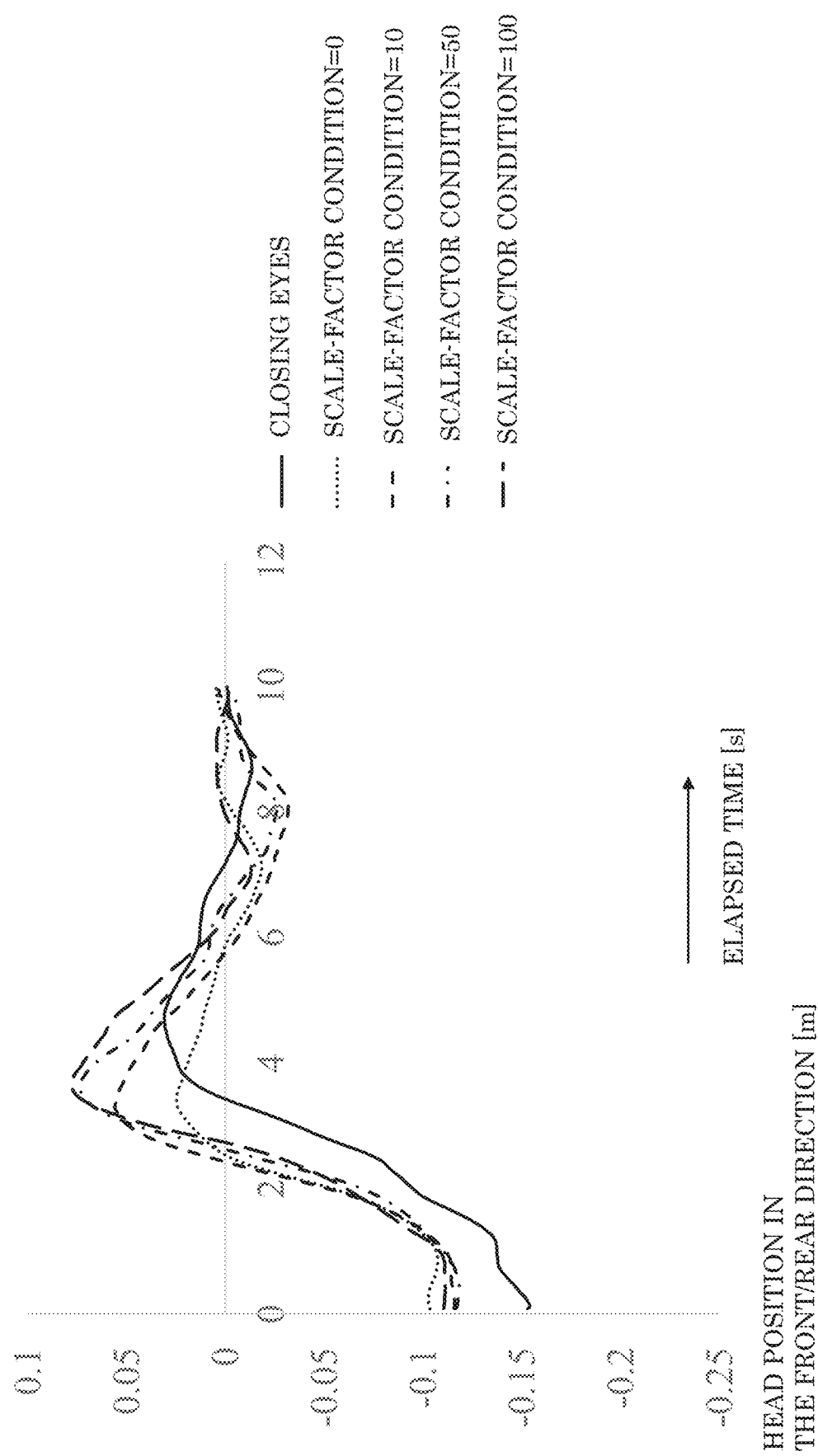
FIG. 15 is a graph showing a change of the head position in the front/rear direction of subject 1 in Experiment 2.
Figure 16:
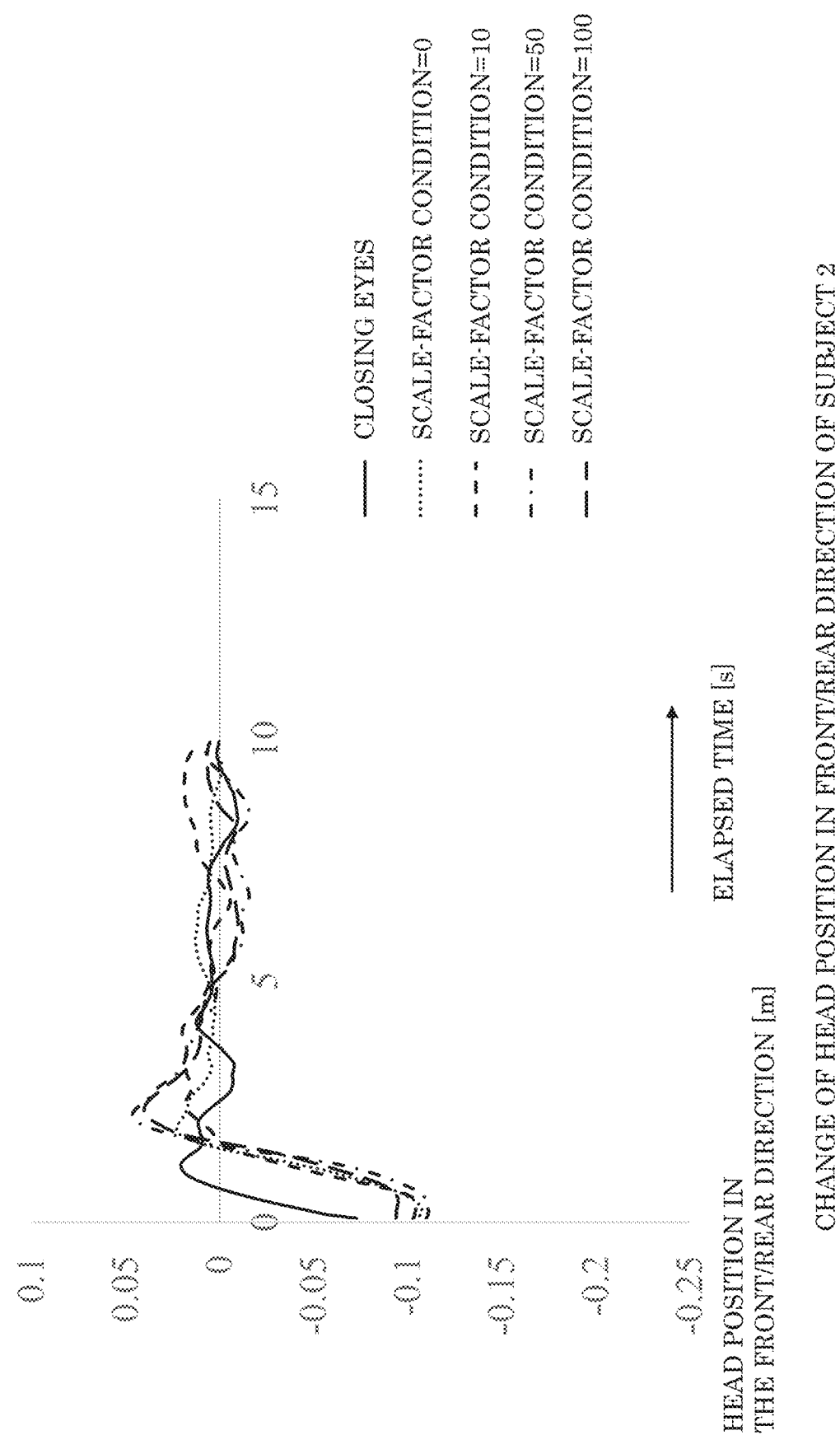
FIG. 16 is a graph showing a change of the head position in the front/rear direction of subject 2 in Experiment 2.
Figure 17:
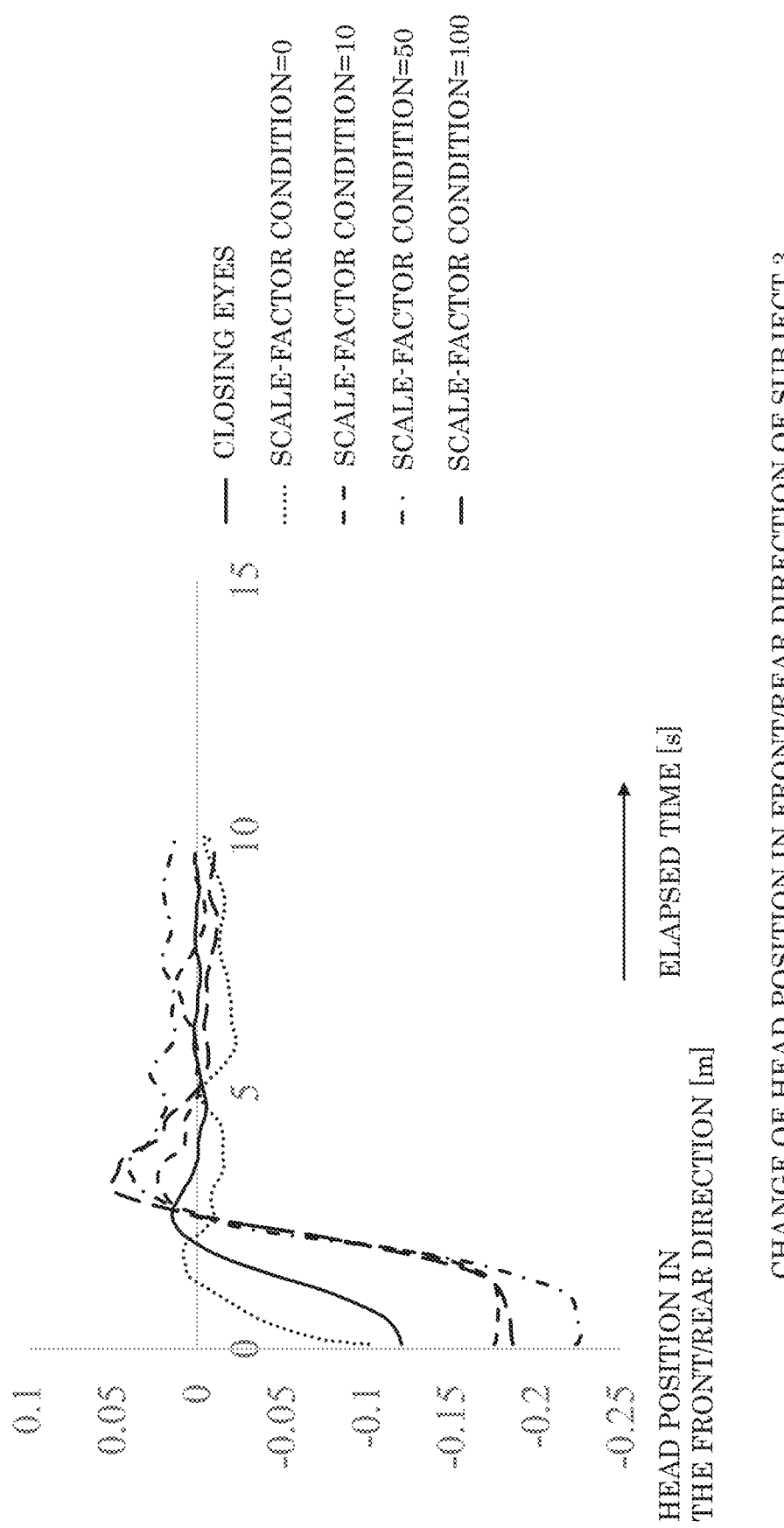
FIG. 17 is a graph showing a change of the head position in the front/rear direction of subject 3 in Experiment 2.

Similarly to Experiment 1, a participant of the experiment wore a HMD to observe an image simulated with a computer. The experiment was started from the position of inclining the upper body backward. The participant was asked to face forward and raise the body from the starting position to return to the upright position. The participant was asked to stand in the Romberg's upright position to control their motion. The presented image was black/white stripes, and a floor image that moved at the speed proportional to the head speed was presented as the visual stimulus in the HMD. In Experiment 2, the participant was asked to try five patterns, including closing eyes, scale-factor condition=0, scale-factor condition=10, scale-factor condition=50, and scale-factor condition=100 for 10 seconds. The number of the participants was three, and they were healthy men in their 20s to 30s. FIGS. 15, 16 and 17 show the head-motion result for these subjects. These graphs show the position of the head (vertical axis) in the front/rear direction (x direction) versus the elapsed time (horizontal axis). The origin is the head position of the participant standing upright, and positive and negative correspond to the front and the rear, respectively.

FIG. 15, FIG. 16, and FIG. 17 show that the forward head-swaying to raise the upper body at the start of the experiment was larger in the visual stimulus of the scale-factor condition=10, the scale-factor condition=50, and the scale-factor condition=100 than in the closing eyes and the scale-factor condition=0. However, the scale-factor conditions recording the largest swaying width varied from one subject to another. They were the scale-factor condition=100 for subject 1, the scale-factor condition=50 was for subject 2, and the scale-factor condition=100 for subject 3. This is because the backward inclination of the upper body to start the experiment or the speed of swaying the body (the head) forward and backward varied from one subject to another. The experiment gave the visual stimulus at the speed proportional to the head speed. This means that a subject moving the head more speedily will observe a visual stimulus of the floor pattern moving more speedily even under the same scale-factor condition. Specifically subject 1 and subject 2 observed visual stimuli at different speeds under the same scale-factor condition=100, and this differentiated the scale factor conditions recording the largest swaying width between these subjects.

The effect of stepping forward was not found in this experiment, and the subjects ended to have the upright state in the experiment. Presumably the reason for this is the instruction to ask them to return to the upright position. Although this instruction was for sufficient swaying widths, this instruction may interfere with an increase in the amplitude.

(Experiment 3)

Experiment 2 confirms that the swaying width of the head as well as at least the speed have to be controlled to find the effective visual stimulus for stepping forward. Based on this, Experiment 3 controlled the forward/backward swaying width to keep the swaying width of the head constant. The experiment also controlled the speed to keep the period constant. Under this environment, the experiment examined a scale-factor condition of the visual stimulus to induce the effective body swaying for stepping forward.

Figure 18:
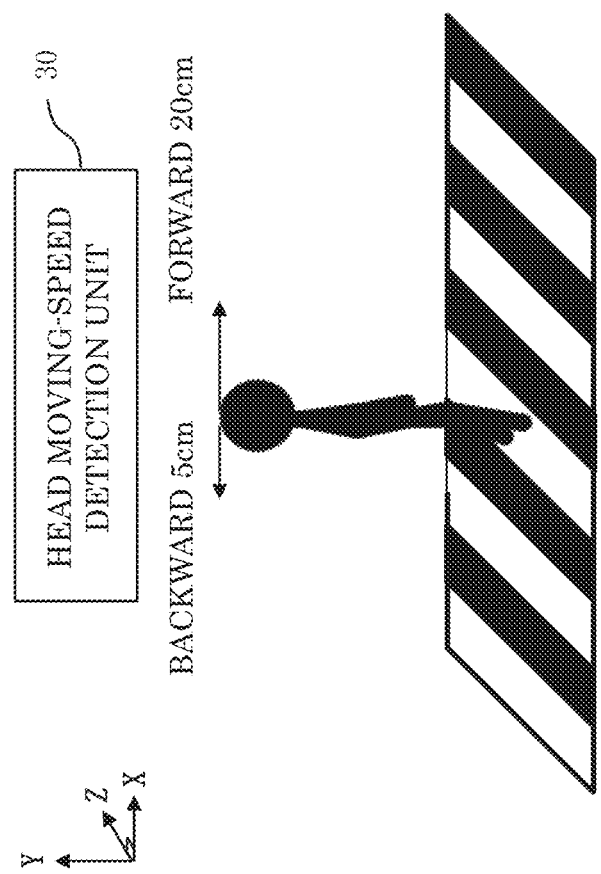
FIG. 18 shows an image of Experiment 3, and shows the amplitude condition for a sound source 1.

Similarly to Experiments 1 and 2, a participant of Experiment 3 wore a HUD to observe an image simulated with a computer. As shown in FIG. 18, sound was emitted (hereinafter called a sound source 1) when the head position was at 20 cm forward and at 5 cm backward relative to the upright posture (standard position) to control the swaying width. To control the speed, sound was continuously emitted from a metronome (hereinafter called a sound source 2) at 45 bpm (beats per minute) (two-two meter, about 7 seconds per period, about 0.3/Hz). The former configuration to emit the sound when the head position is at 20 cm forward and at 5 cm backward can be implemented measuring the position of the head with a camera to take an image of the head, or using a mechanical structure that emits a sound from a simple mechanical contact at the timing when the head reaches the position. Alternatively the sensor of the HMD as stated above may implement a means for measuring the positions in the front/rear direction (20 cm forward and 5 cm backward) relative to the standard position of the HMD, and a sound emitting unit may be provided to issue sound at the position. The speed may be calculated from the sound-emitting position (20 cm forward and 5 cm backward of the upright position), the timing and the setting period (duration) of the metronome. In this way, a head (viewpoint) moving-speed detection unit 30 can have various configurations, and may be simply configured to include the sound-emitters of the sound sources 1 and 2 that function as the head moving-speed detection unit 30.

In this experiment, the subject was asked to adjust their body-inclining speed repeatedly so that the sound source 1 and the sound source 2 beeped at the forward position at the same time and the sound source 1 and the sound source 2 beeped at the backward position at the same time. At first the subject was asked to repeat the back-and-forth swaying so that sound from the sound source 1 and the sound source 2 concurred while closing their eyes. After the sound concurred consecutively six times, they were asked to open the eyes at the moment where they changed the direction from the backward direction to the forward direction for the first time. The difference between the sound source 1 and the sound source 2 within a predetermined duration, e.g., ¼ period, or shorter (about 0.68 second) was dealt with as the concurrence of the sound. Similarly to Experiments 1 and 2, the presented image was black/white stripes, and a floor image that moved at the speed proportional to the head speed was presented as the visual stimulus in the HMD. The participants were asked to try four patterns, including scale-factor condition=0, scale-factor condition=10, scale-factor condition=50, and scale-factor condition=100. The number of the participants was five, and they were healthy men in their 20s to 30s.

FIGS. 19 to 22 show the result for the conditions to show the magnitude of the head motion. These drawings show the position of the head (vertical axis) in the front/rear direction (x direction) versus the elapsed time (horizontal axis). The time 0 is when the subject opened the eyes, and positive and negative correspond to the front and the rear, respectively.

These drawings show the ideal head motion Gs swaying with the sound source as supplemental graph.

Figure 19:
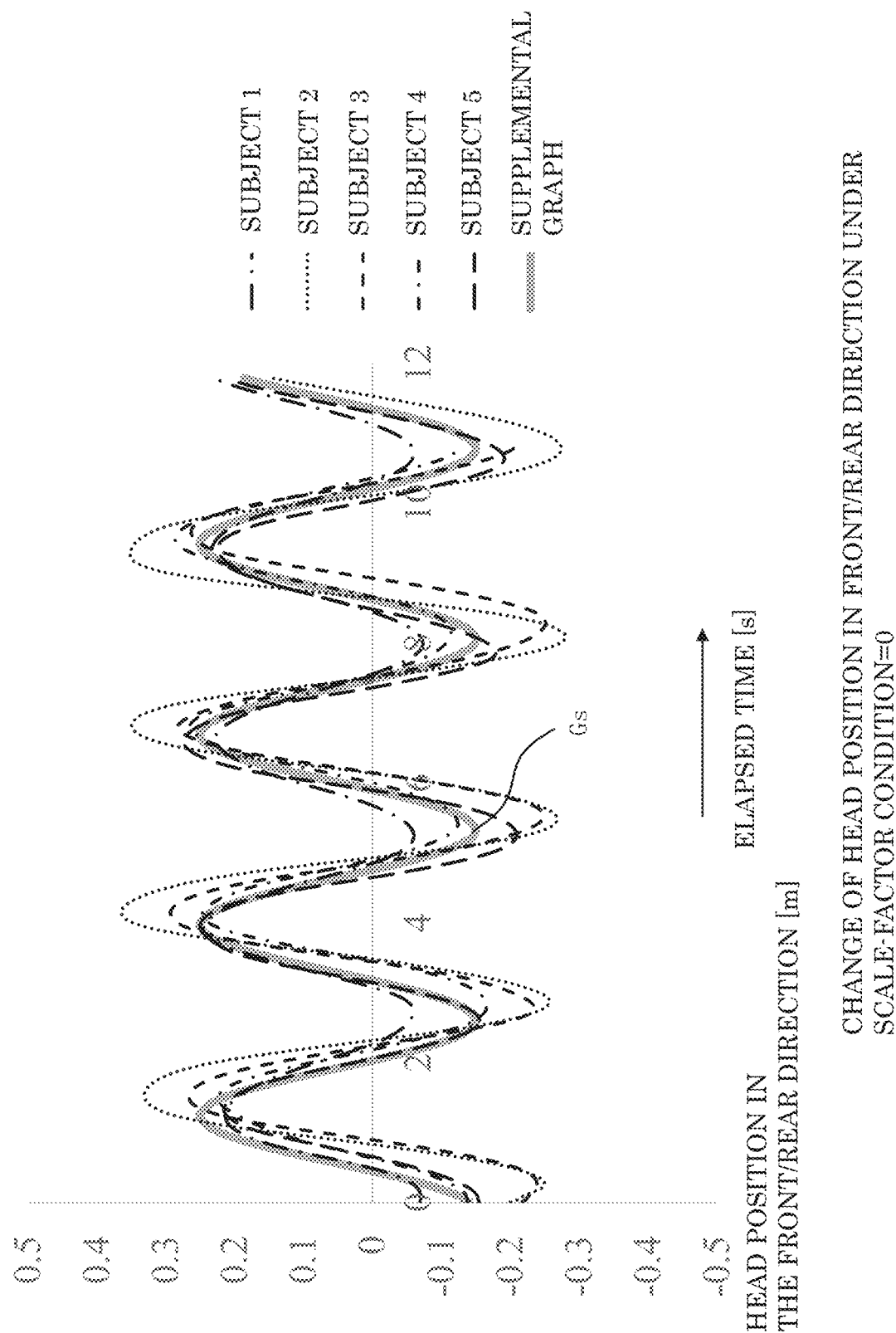
FIG. 19 is a graph showing a change or the head position in the front/rear direction under the scale-factor condition=0 in Experiment 3.
Figure 20:
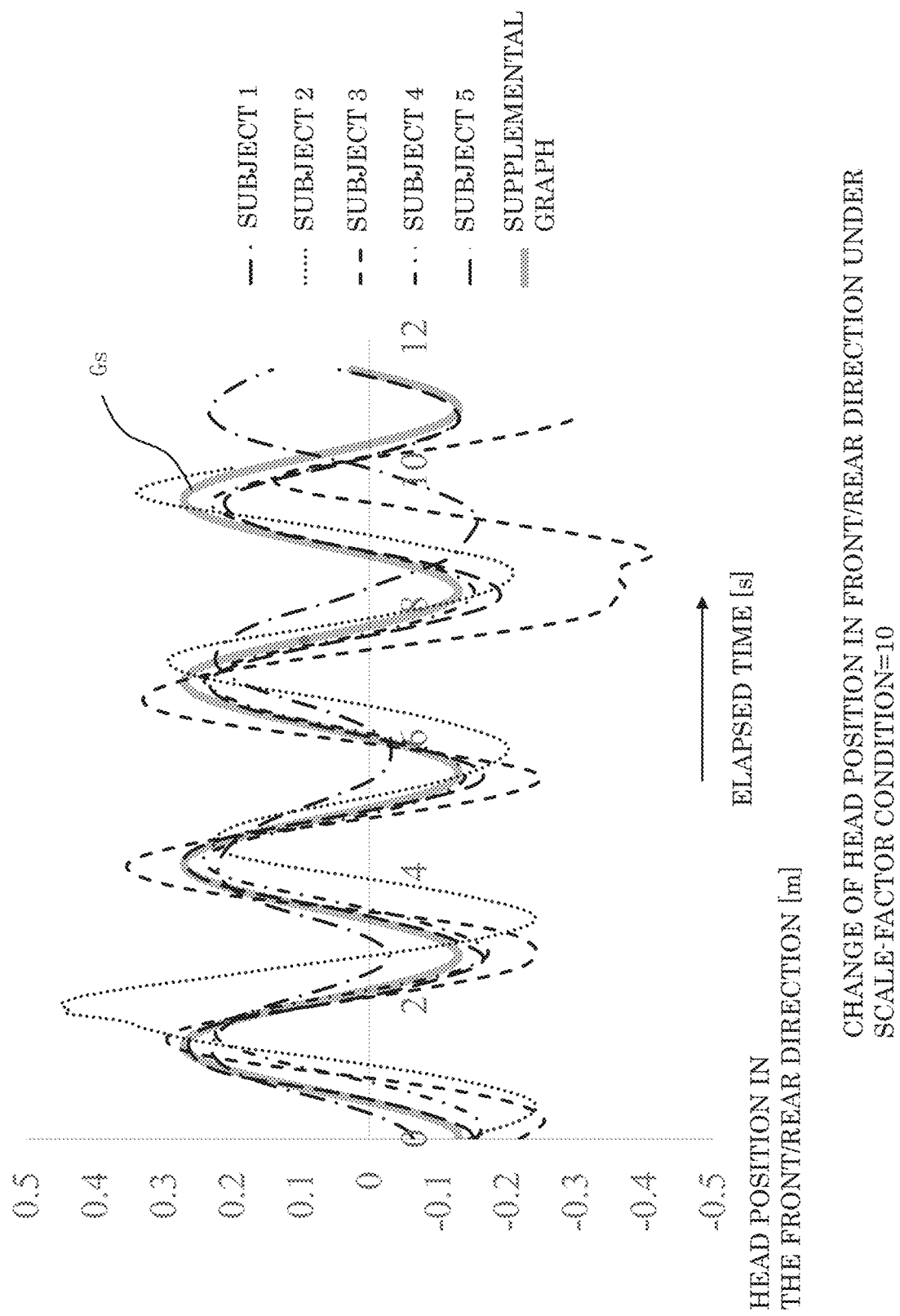
FIG. 20 is a graph showing a change of the head position in the front/rear direction under the scale-factor condition=10 in Experiment 3.
Figure 21:
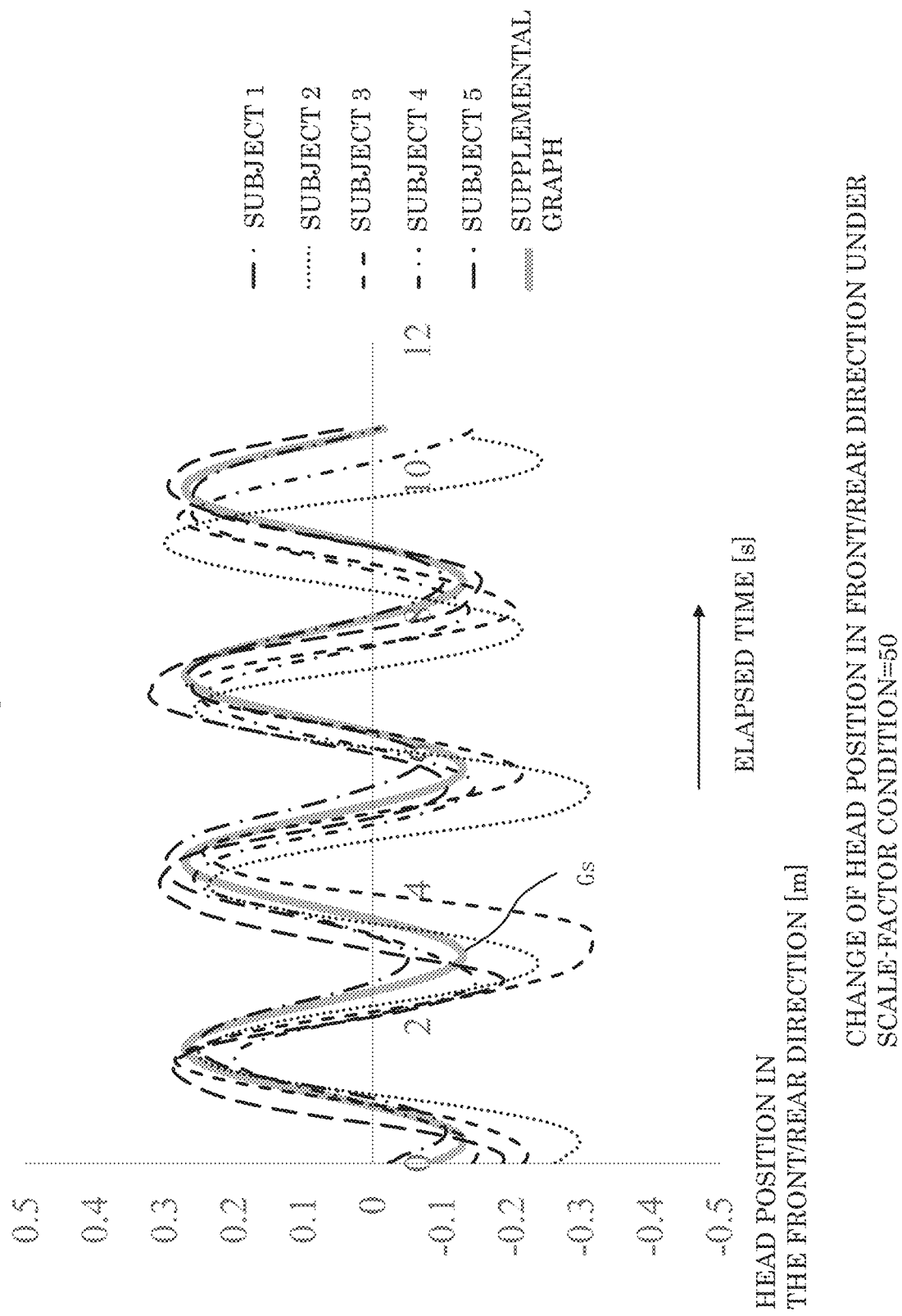
FIG. 21 is a graph showing a change of the head position in the front/rear direction under the scale-factor condition=50 in Experiment 3.
Figure 22:
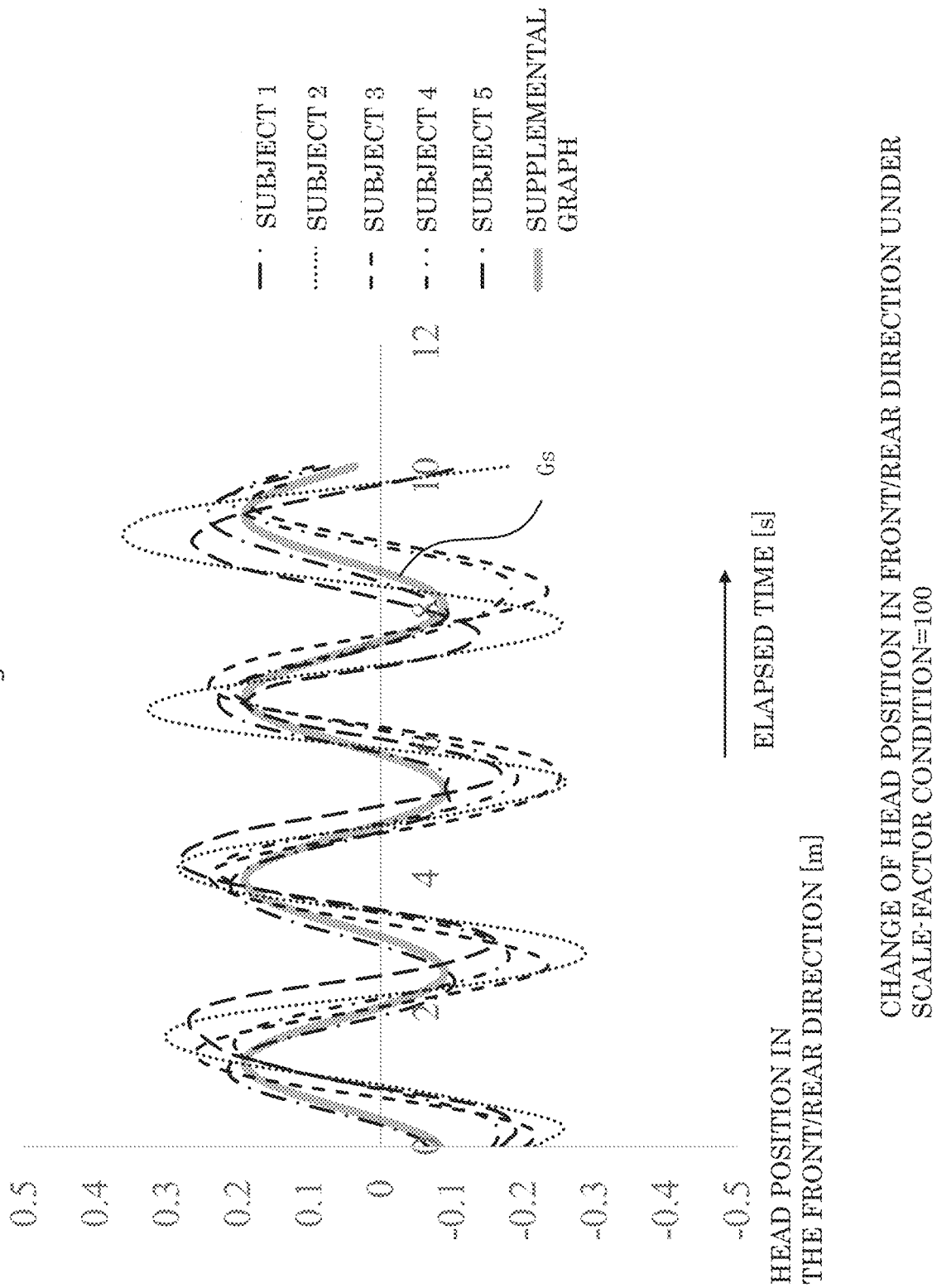
FIG. 22 is a graph showing a change of the head position in the front/rear direction under the scale-factor condition=100 in Experiment 3.

FIG. 19, FIG. 21, and FIG. 22 show that a difference in amplitude found was only about 5 cm among the case of without visual stimulus (FIG. 19), the scale-factor condition=50 (FIG. 21) and the scale-factor condition=100 (FIG. 22), and so any large effect was not found. FIG. 20 shows that visual stimulus of the scale-factor condition=10 caused an increase in amplitude of about 10 cm and a phase shift, and finally caused stepping-off from the position. This confirms that visual stimulus of scale factor condition=10 is effective compared to other visual stimuli (scale-factor condition=50, and scale-factor condition=100). The phenomenon of stepping-off from the position can be an aid for the gait, and so this visual stimulus will induce an effective body swaying for the stepping forward.

(Experiment 4)

Figure 23:
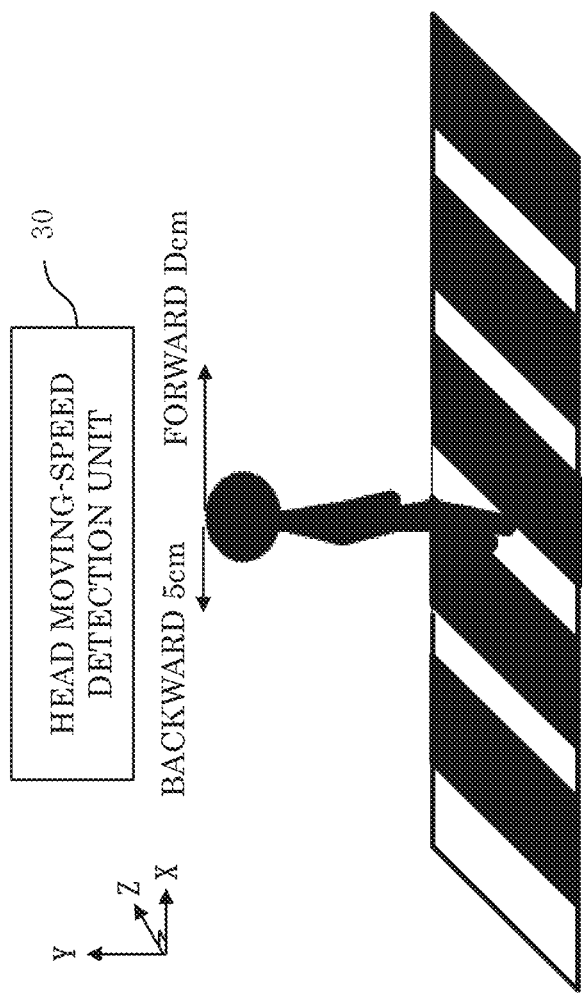
FIG. 23 shows an image of Experiment 4, and shows the amplitude condition for a sound source 1.
Figure 24:
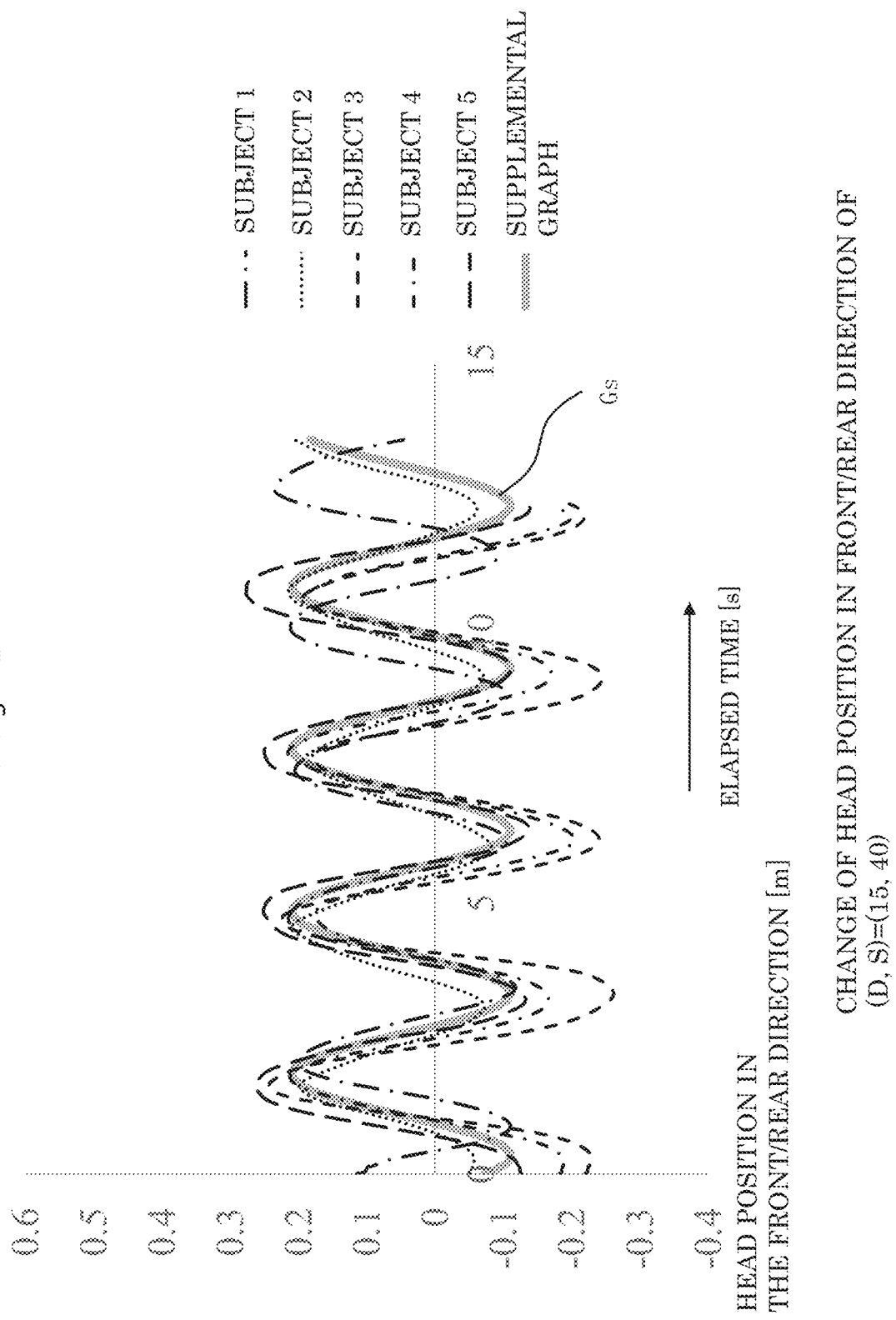
FIG. 24 is a graph showing a change of the head position in the front/rear direction of (D, S)=(15, 40) in Experiment 4.
Figure 25:
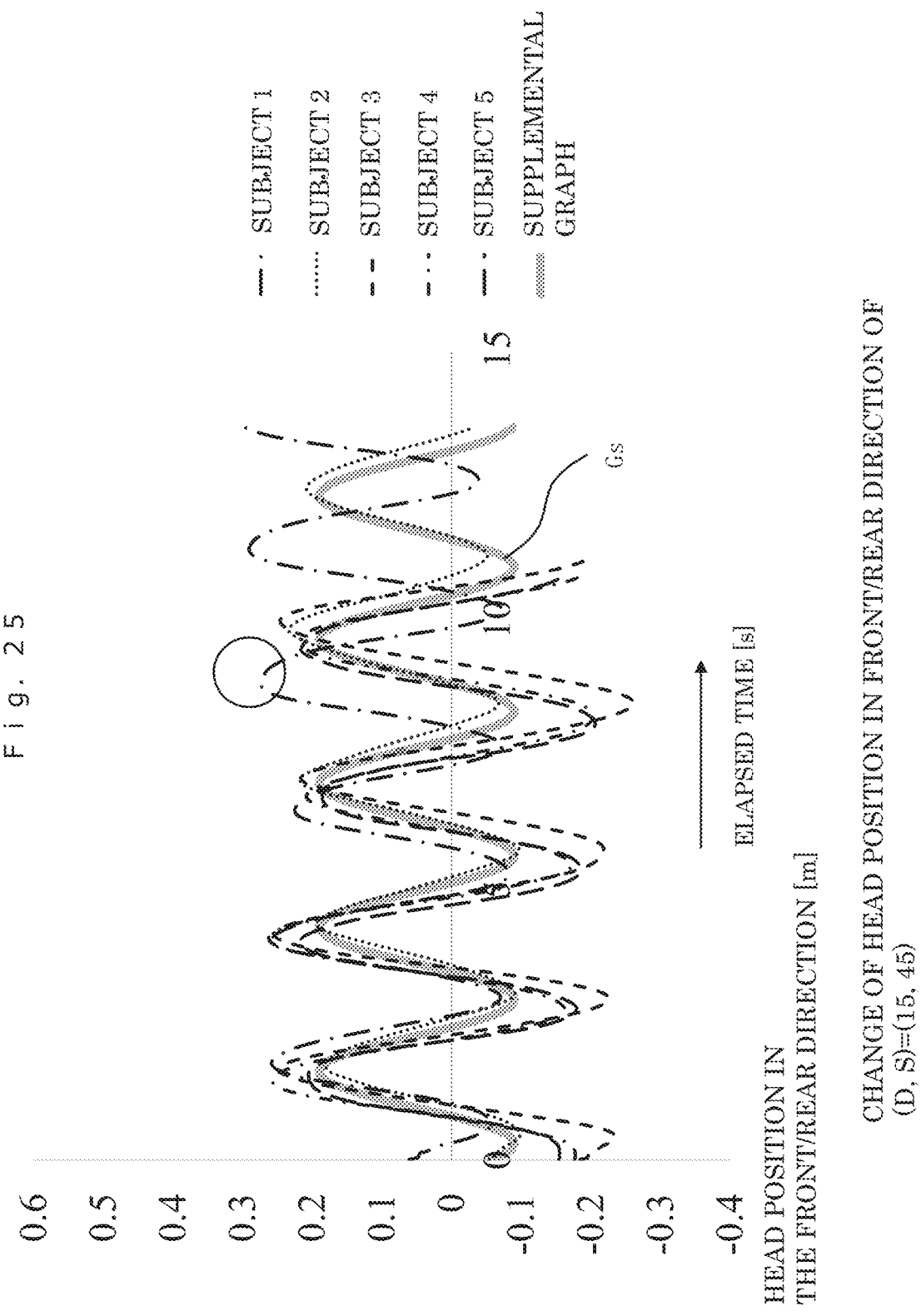
FIG. 25 is a graph showing a change of the head position in the front/rear direction of (D, S)=(15, 45) in Experiment 4.
Figure 26:
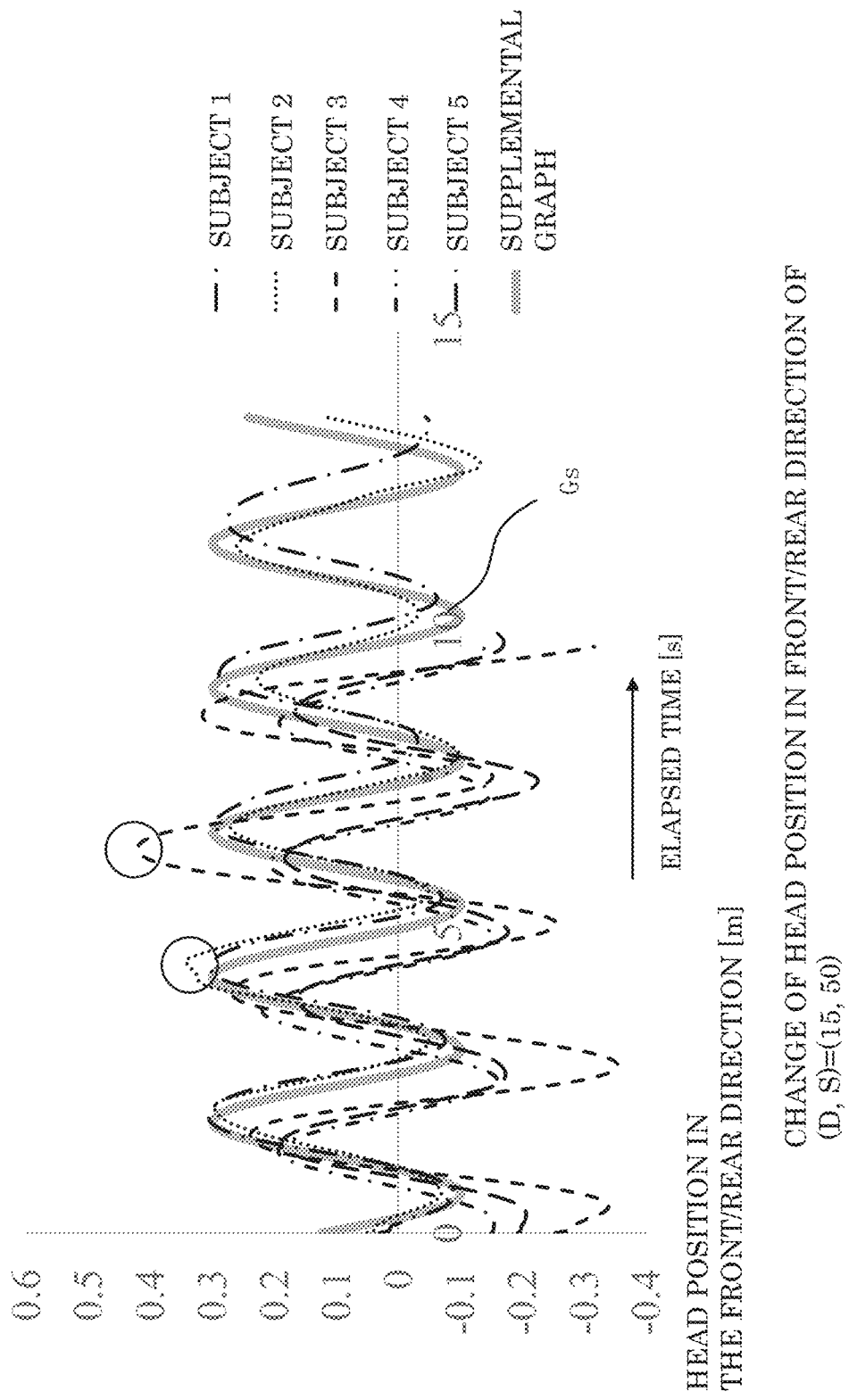
FIG. 26 is a graph showing a change of the head position in the front/rear direction of (D, S)=(15, 50) in Experiment 4.
Figure 27:
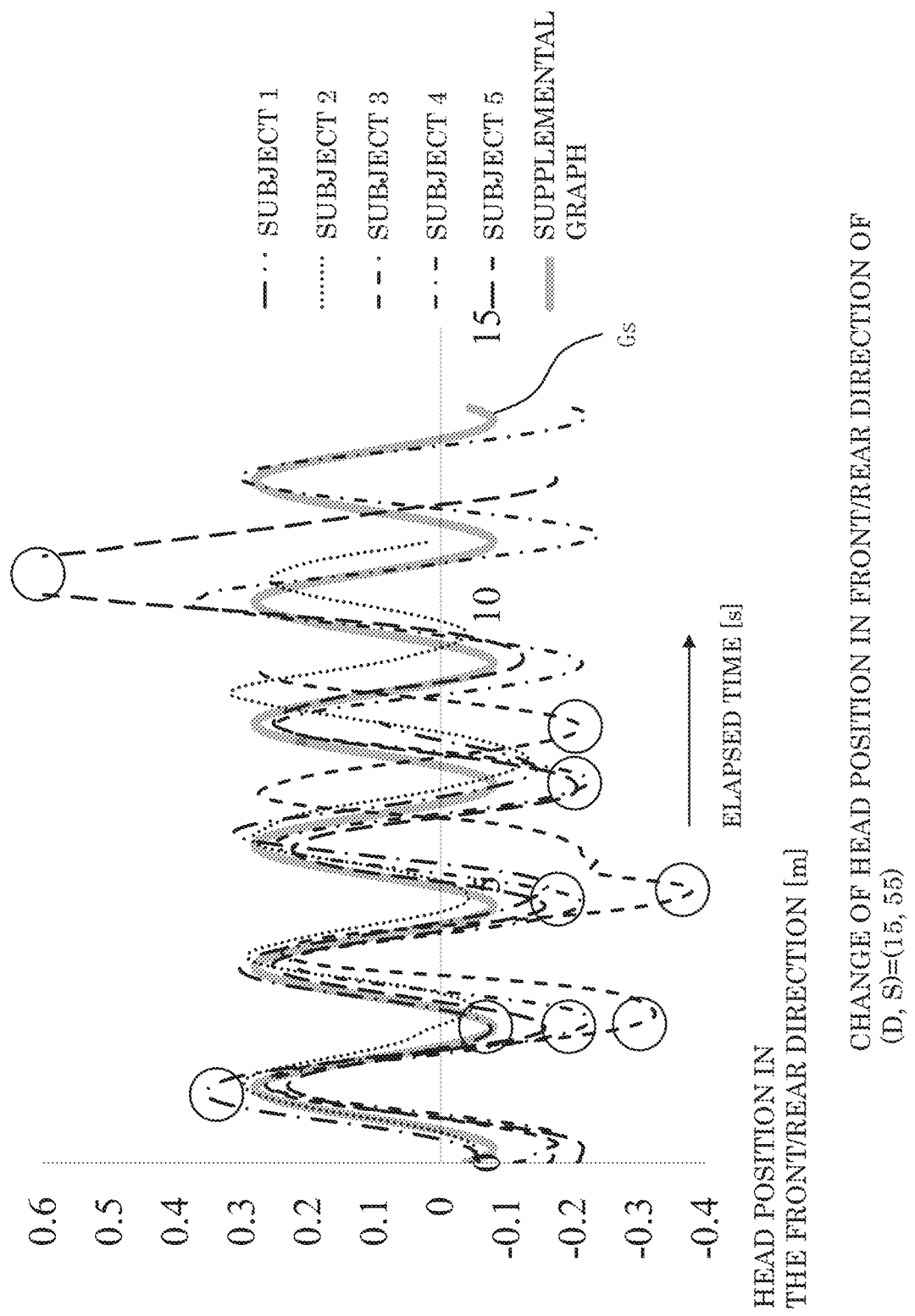
FIG. 27 is a graph showing a change of the head position in the front/rear direction of (D, S)=(15, 55) in Experiment 4.
Figure 28:
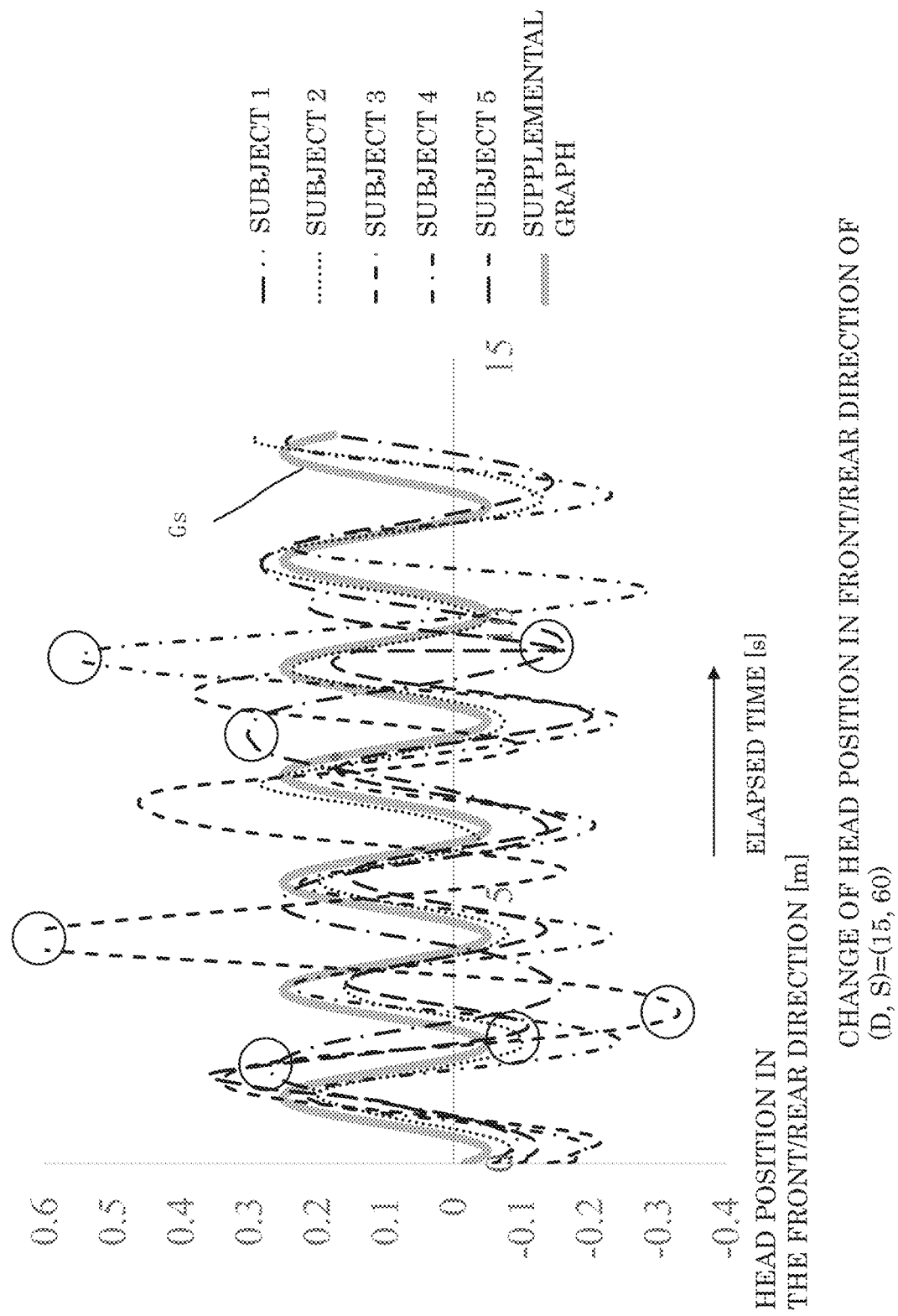
FIG. 28 is a graph showing a change of the head position in the front/rear direction of (D, S)=(15, 60) in Experiment 4.
Figure 29:
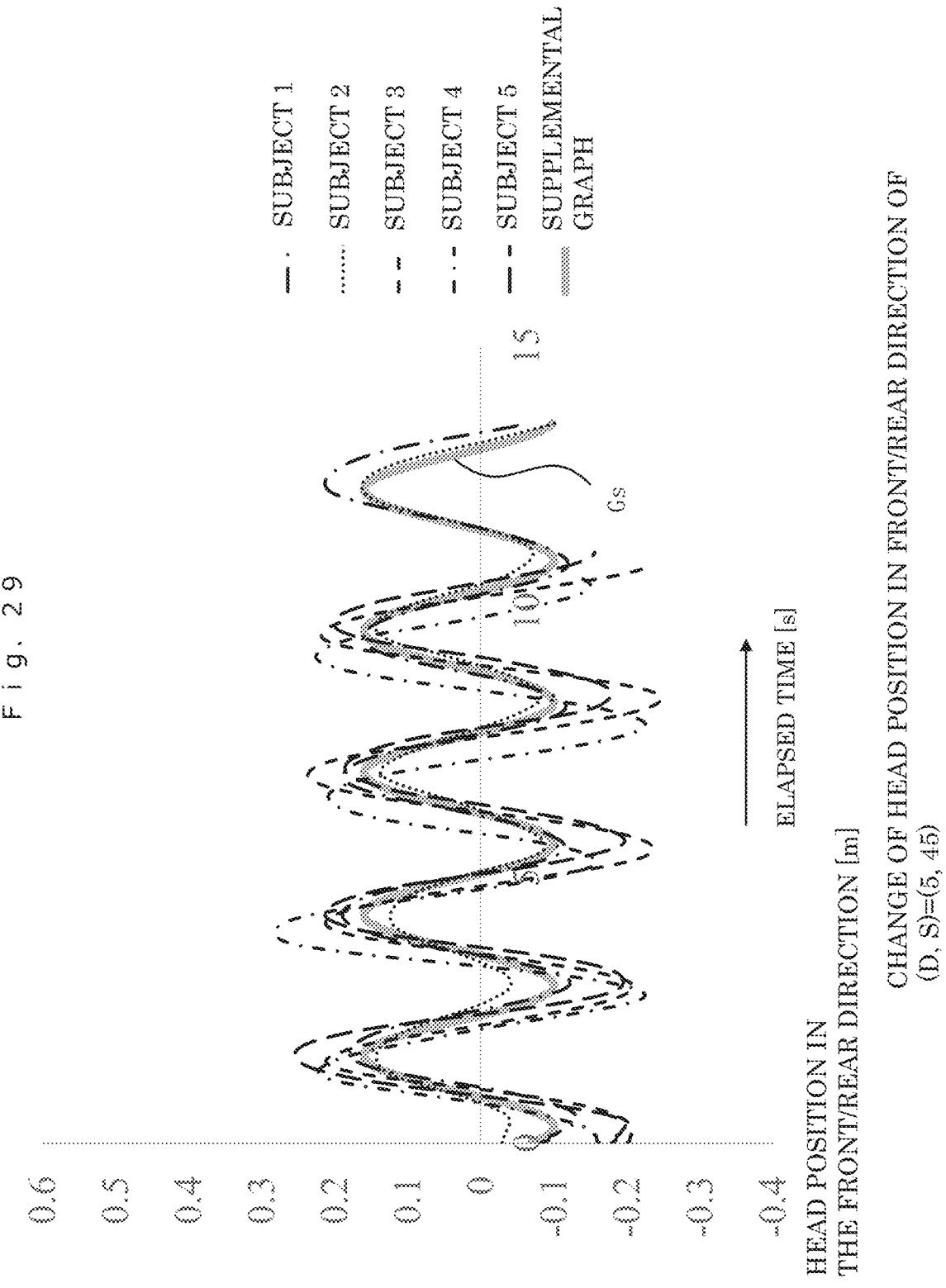
FIG. 29 is a graph showing a change of the head position in the front/rear direction of (D, S)=(5, 45) in Experiment 4.
Figure 30:
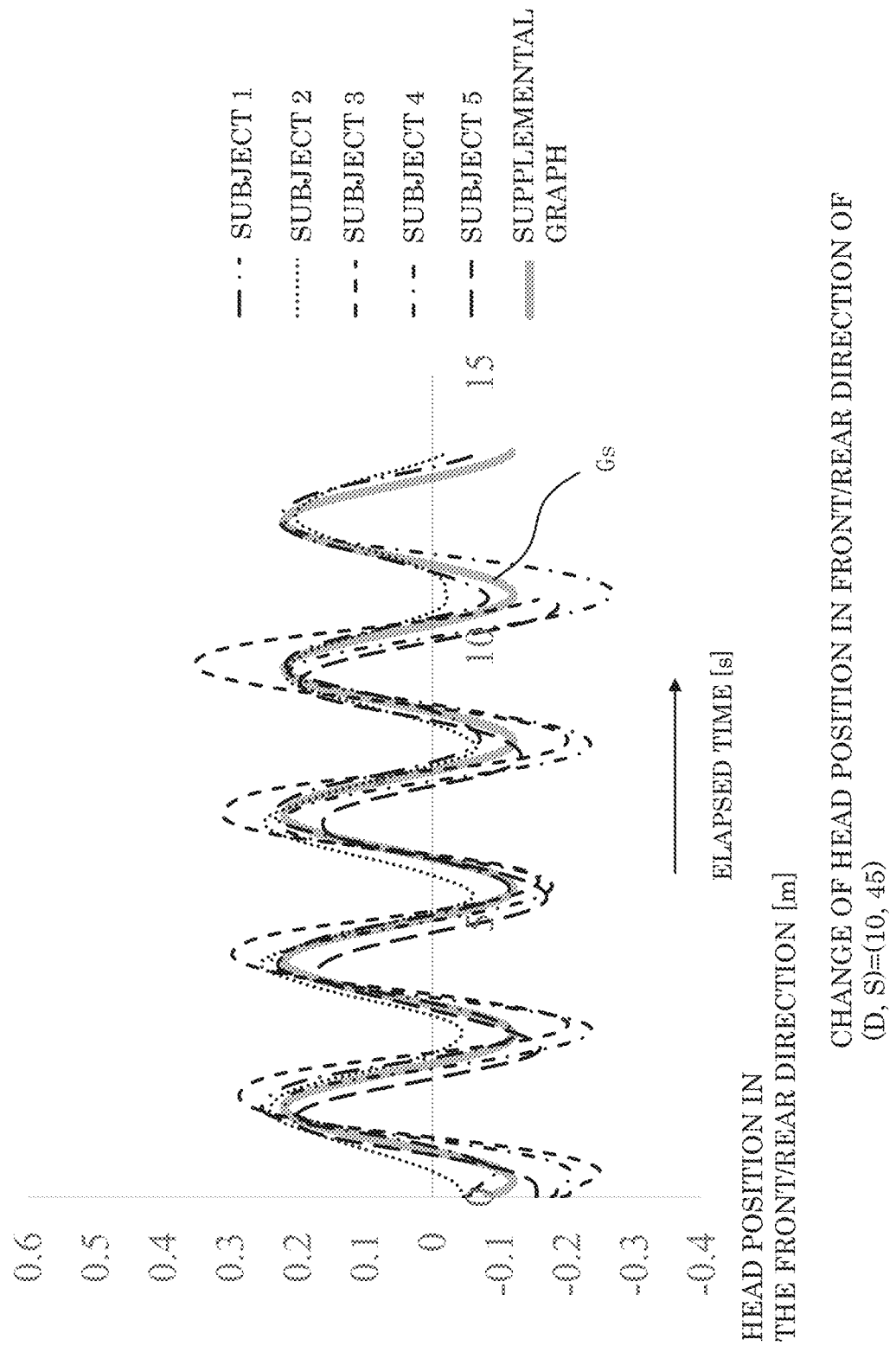
FIG. 30 is a graph showing a change of the head position in the front/rear direction of (D, S)=(10, 45) in Experiment 4.
Figure 31:
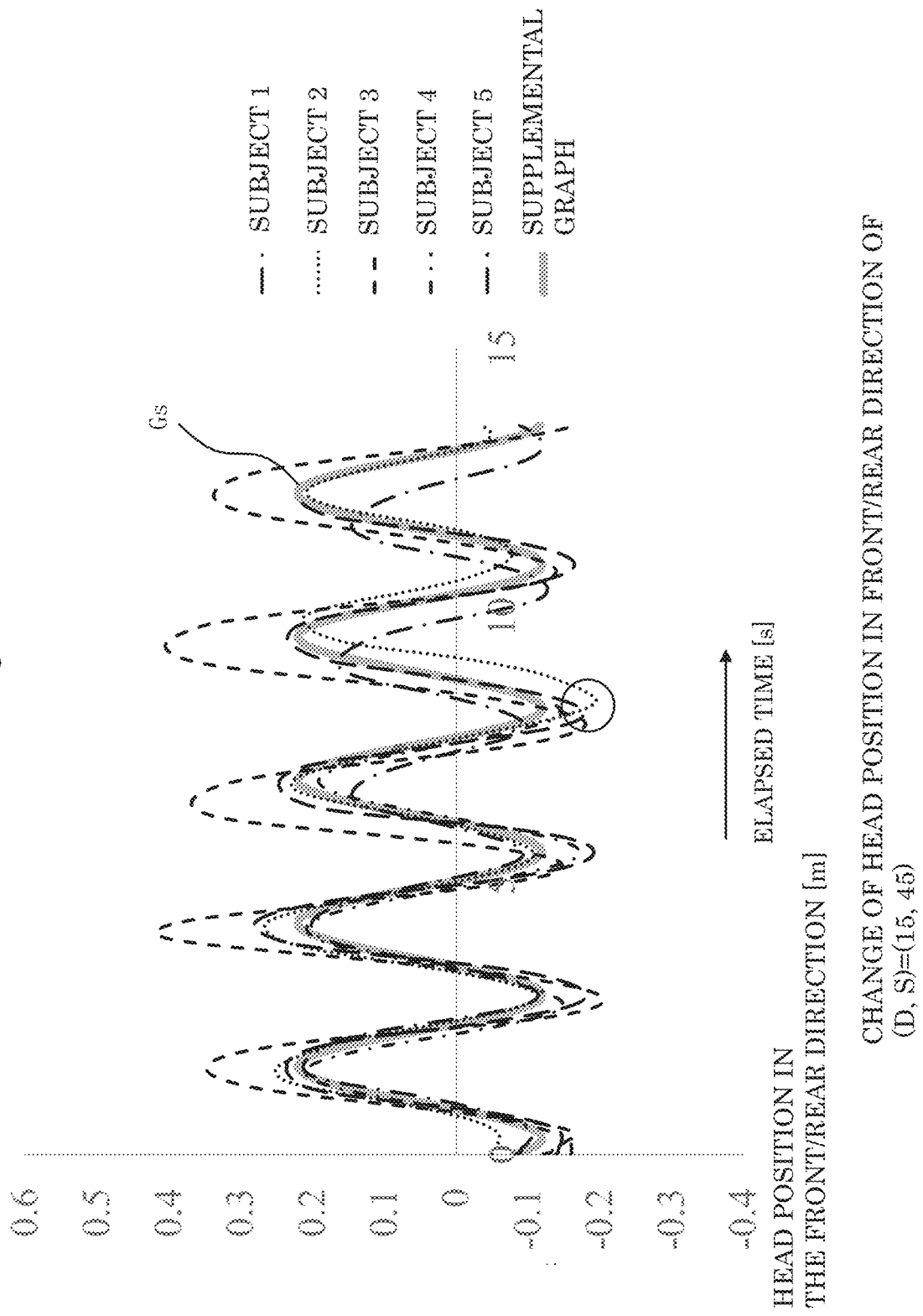
FIG. 31 is a graph showing a change of the head position in the front/rear direction of (D, 3)=(15, 45) in Experiment 4.
Figure 32:
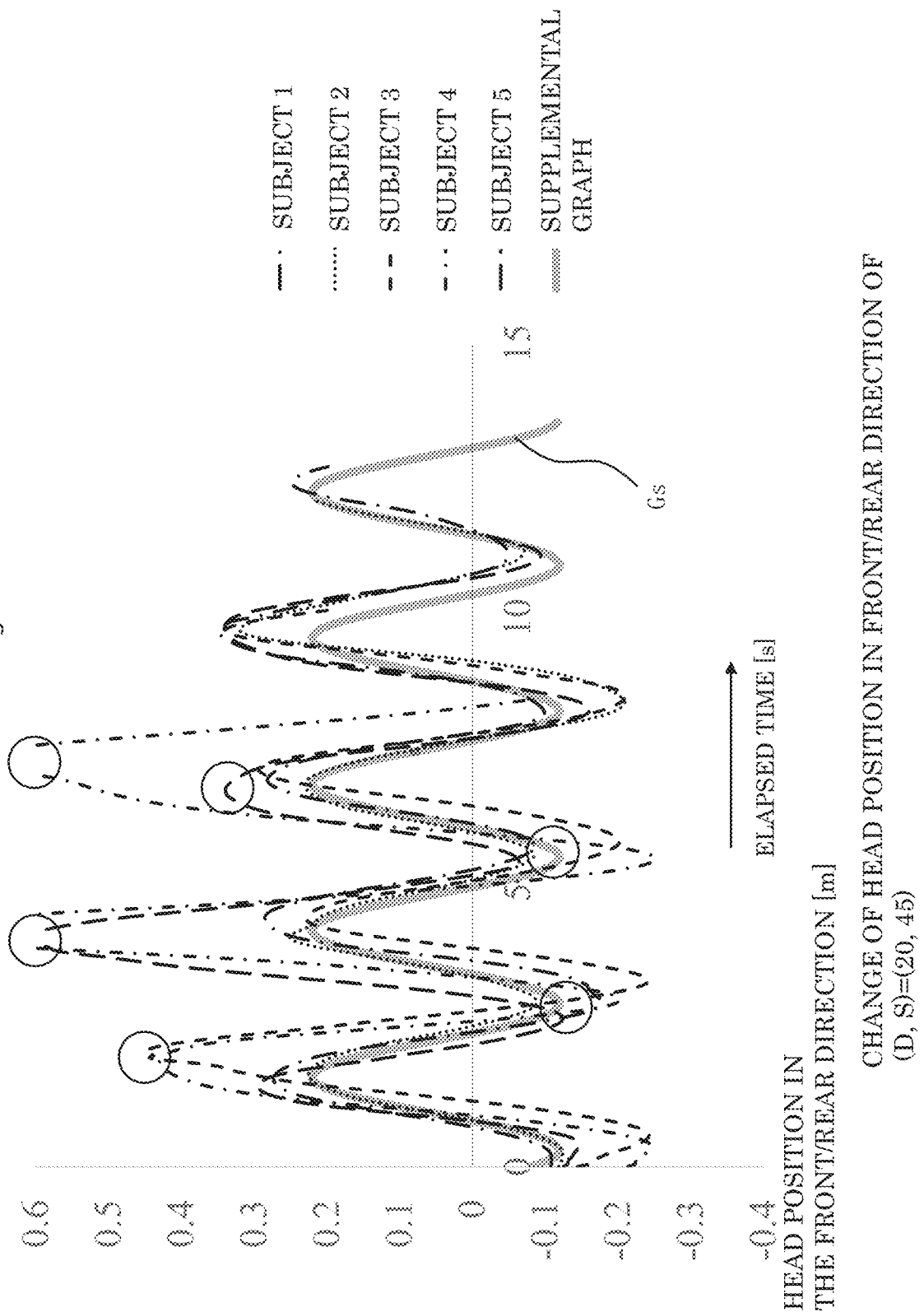
FIG. 32 is a graph showing a change of the head position in the front/rear direction of (D, S)=(20, 45) in Experiment 4.

Experiment 3 confirms that the scale-factor condition=10 is effective. Experiment 3 controlled the swaying width and speed of the head, and so more effective swaying widths and speeds were still unknown Based on this, Experiment 4 examined a swaying, width and a speed that induced a more effective body swaying for stepping forward. Similarly to Experiments 1, 2, and 3, a participant of the experiment wore a HMD to observe an image simulated with a computer. Sound was emitted (hereinafter called a sound source 1) when the head position was at D cm forward and at 5 cm backward (FIG. 23). To control the speed, sound was continuously emitted from a metronome (hereinafter called a sound source 2) at S bpm (beats per minute) (two-two meter).

In this experiment, the subject was asked to adjust their body-inclining speed repeatedly so that the sound source 1 and the sound source 2 beeped at the forward position at the same time and the sound source 1 and the sound source 2 beeped at the backward position at the same time. At first the subject was asked to repeat the back-and-forth swaying so that sound form the sound source 1 and the sound source 2 concurred while closing their eyes. After the sound concurred consecutively six times, they were asked to open the eyes at the moment when they changed the direction from the backward direction to the forward direction for the first time. The difference between the sound source 1 and the sound source 2 within ¼ period or shorter was dealt with as the concurrence of the sound. Similarly to Experiments 1, 2 and 3, the presented image was black/white stripes, and a floor image that moved at the speed proportional to the head speed was presented as the visual stimulus in the HMD. The speed was fixed at the scale-factor condition=10. As shown in Table 1, the patterns of this experiment were ten in total. The number of the participants was five, and they were healthy men in their 20s.

TABLE 1

| Amplitude | Speed | Conditions |
|---|---|---|
| fixed (D = 15) | variable S | S = {40, 45, 50, 55, 60} |
| variable D | fixed (S = 45) | D = {5, 10, 15, 20, 25} |

FIGS. 24 to 33 show the result for the conditions to show the magnitude of the head motion. These graphs show the position of the head (vertical axis) in the front/rear direction (x direction) versus the elapsed time (horizontal axis). The time 0 is when the subject opened the eyes, and positive and negative correspond to the front and the rear, respectively. These drawings show the ideal head motion Gs swaying with the sound source as supplemental graph. In these drawings, circles indicate the timing when the subject stepped off from the position.

FIG. 24 to FIG. 28 show that the swaying speed of 40 bpm to 50 bpm just had an effect of a slight delay in phase and an increase in the amplitude (stepping-off from the position was found only in two cases), and the swaying speed increased to 55 bpm and 60 bpm had an effect that all of the subjects stepped off from the position. This shows that the swaying speed was more effective in 55 bpm or more than in 40 bpm to 50 bpm, and the speed of 55 bpm or more induced an effective body swaying for stepping forward, because the phenomenon of stepping-off from the position can be an aid for the gait. FIG. 29 to FIG. 33 show that the forward-swaying width of 5 cm to 15 cm just had an effect of a slight delay in phase and an increase in the amplitude (stepping-off from the position was found only one case), and the forward-swaying width increased to 20 cm and 25 cm had an effect that all of the subjects stepped off from the position. This shows that the forward-swaying width was more effective in 20 cm or more than in 5 cm to 15 cm, and the forward-swaying width of 20 cm or more induced an effective body swaying for stepping forward, because the phenomenon of stepping-off from the position can be an aid for the gait.

These experiments confirm that visual stimuli at the speed proportional to the head-moving speed in the same direction as the head-moving direction led to the stepping-forward of the subject when the visual stimulus at the speed of the scale-factor condition=10 was given to the subject. Stepping-forward was not found under the conditions of the scale-factor conditions=0, 50, and 100, and the experiments show that the visual stimulus at the 10-times speed of the head speed is effective. Experiment 4 about the body-swaying speed and the swaying-width shows that stepping-forward occurred at the speed of 55 bpm or more for the swaying width of 15 cm and at the swaying width of 20 cm or more for the speed of 45 bpm.

These values are converted into the moving speed of visual stimulus (the moving speed of the stripes shown on the floor) for generalization. Under the conditions of the scale-factor condition=n, the forward-swaying width of D cm, the backward-swaying width of 5 cm, and the sound source 2 (metronome) of S bpm (beats per minute) and two-two meter, the amplitude motion of the head is considered as a linear motion. In this case, the amplitude A of one period can be obtained by adding the backward amplitude of 5 cm relative to the standard point to D cm and then by unit conversion, i.e., by the following equation.

$$A=\{(D+5)/2\}/100(m) \qquad \text{(Expression 17)}.$$

Since the sound was S bpm of two-two meter, the period T can be represented by the following equation.

$$T=2(60/S)(s) \qquad \text{(Expression 18)}.$$

Therefore the moving speed of the floor image can be represented as follows.

$$2n\pi A/T(m/s) \qquad \text{(Expression 19)}.$$

Substituting of the conditions in Experiment 4 into Expression 19 gives Table 2.

TABLE 2

| conditions (D, S) | maximum speed of head motion (m/s) |vx| | floor maximum speed (m/s) |vx'| |
|---|---|---|
| (15, 40) | 0.209 | 2.094 |
| (15, 45) | 0.236 | 2.356 * |

TABLE 2-continued

| conditions (D, S) | maximum speed of head motion (m/s) \|vx\| | floor maximum speed (m/s) \|vx'\| | |
|---|---|---|---|
| (15, 50) | 0.262 | 2.618 | * |
| (15, 55) | 0.288 | 2.880 | ** |
| (15, 60) | 0.314 | 3.142 | ** |
| (5, 45) | 0.118 | 1.178 | |
| (10, 45) | 0.177 | 1.767 | |
| (15, 45) | 0.236 | 2.356 | * |
| (20, 45) | 0.295 | 2.945 | ** |
| (25, 45) | 0.353 | 3.534 | ** |

Table 4.1 Floor Speed Various Conditions in Experiment 4

In Table 2, the conditions without * are the case where no stepping-forward was found. The conditions with * are the case where some subjects stepped forward, and the conditions with ** are the case where all of the subjects stepped forward Table 2 shows that the speed condition of the head motion is preferably about 0.23 m/s to 0.36 m/s (with *), and is more preferably about 0.28 m/s to 0.33 m/s (with **). This means that the scale-factor condition=10 is effective, and when the maximum speed of the head motion exceeds about 0.28 (m/s), meaning that the floor speed of about 2.8 (m/s) or more, this achieves a visual stimulus that induces the body swaying well for stepping forward. In this way, when a visual stimulus meets these conditions, the visual stimulus is able to induce a body swaying for stepping forward.

Such a pattern changing sheet is applicable to a walking inducing or guidance sheet in medical practice or at home for Parkinson's disease patients or for general gait rehabilitation. This sheet is applicable to public transportation facility as well. In one example, this sheet may be used in the site of passengers dashing for a train, for example, which may cause disruption or danger, such as the collision of the passengers, so as to encourage the passengers to reduce the walking speed and avoid such a situation. In this case, the present invention can be used for the expected effect of generating a body swaying in the passengers to reduce the walking speed. Such a pattern changing sheet may be attached to side walls of roads or tunnels to encourage drivers of vehicles to reduce the driving speed.

In an embodiment including a parallax barrier of the present invention, an optical element layer may be a light-blocking sheet having slit-like light-transmitting parts bored with a first pitch, and a pattern layer having a gradation pattern may be opposed to the optical element layer at a predetermined distance away from the optical element layer with a transparent layer therebetween, for example.

In the above embodiment, the optical elements 11 and the gradation pattern 21 are lines arranged in the left-right direction that is the bus-line direction. Instead, a part of the optical elements 11 and the graduation pattern 21 in the left-right direction, e.g., at least one of the left and the right may intersect with the bus-line direction. In one example, the optical elements 11 and the gradation pattern 21 as a whole may have a predetermined curvature, and the intersecting optical elements 11 and gradation pattern 21 as stated above may connect on the left and the right. In another example, the optical elements 11 and the patterned layer 20 are the same as stated above, and the interval of the dots of the gradation pattern 21 may be adjusted at a desired part to change the width of bright parts and dark parts in the display pattern or to partially change the moving speed (moving scale-factor) of the display pattern. Such a configuration enables the vection effect not only in the pitch direction but also in the direction intersecting the pitch direction (outward to the left or right), and enables adjustment of intensity of the vection (magnitude of the speed scale-factor) as needed.

As described above, a pattern changing sheet according to the present invention has a display pattern as a gradation pattern to be observed from a viewpoint of a viewer, the display pattern progressing at a predetermined speed scale-factor of movement of the viewpoint. Preferably the pattern changing sheet includes: an optical element layer including optical elements at least in number corresponding to one wavelength of the pattern changing sheet, the optical elements being disposed with a first pitch in a direction orthogonal to the optical axis of the optical elements, each optical element having a light-transmitting part in a plane having a direction of disposing the optical elements and the direction of the optical axis, the light-transmitting part enabling the viewer to view inside of the optical element layer from a plurality of directions intersecting with the optical axis direction; and a pattern layer disposed on a rear face of the light-transmitting part of the disposed optical elements to be opposed to the optical elements, the pattern layer having a gradation pattern having pixels assigned at positions on the rear face of the light-transmitting part so as to allow the viewer to view the pixels in the plurality of directions from the viewpoint to the optical elements, the display pattern of the one wavelength is expressed based on the pixels in each optical element, each pixel being assigned to corresponding direction of the plurality of directions. The number of the pixels in the gradation pattern is set at a predetermined number so that, as the viewpoint moves while sequentially changing into an adjacent direction of the plurality of directions, the display pattern at the predetermined speed scale progresses repeatedly the predetermined number of times so as to progress by the one wavelength.

According to the present invention, when a viewer observes the optical element layer from a viewpoint, the viewer observes a pixel located at the observing angle via the light-transmitting part of each optical element, so that these pixels connect in the view in the disposing direction of the optical elements to be expressed as the display pattern. As the viewpoint moves, the display pattern of one wavelength sequentially progresses at the predetermined speed scale-factor in the disposing direction, and this induces vection. In this configuration, the first pitch and the wavelength of the display pattern have no dependency and can be individually designed. The wavelength of the display pattern and the speed scale-factor relative to the moving speed of the viewpoint also have no dependency, and can be individually designed. The present invention therefore creates and provides a pattern changing sheet having a high degree of freedom and depending on the intended use. The number of the gradation pattern formed in the pattern layer is not limited to the number corresponding to the display pattern of one wavelength, and the display pattern corresponding to a plurality of wavelengths may be formed in the disposing direction.

The gradation pattern may satisfy the condition expressed by Expression 1.

[Mathematical 16]

$$n = \left\lfloor \frac{W}{L_0^*} \right\rfloor, \; m = \left\lfloor \frac{\Delta W}{L_0^*} \right\rfloor, \; j = \left\lfloor \frac{2\gamma\rho H}{DL_0^*} \tan\frac{\alpha}{2} \right\rfloor \quad \text{(Expression 1)}$$

In this Expression,
dW<W/2, j<n/2.
⌊ ⌋ denotes floor functions.

Design values n, m, and j are integers, and j<n/2, m<n.

W denotes the wavelength, ΔW denotes the length of a bright part, and $L_0^* = (1+h/H) \cdot L_0$. $L_0$ denotes the first pitch, H denotes a distance to the viewpoint, and ii denotes the thickness of the optical elements.

D denotes the resolution, γ denotes the speed scale-factor, ρ denotes the density of bus lines, and a denotes an expected angle.

This configuration allows individual designing of the wavelength, the length of the pattern, and the speed scale-factor by Expression 1. Since the virtual bus-line pitch and the bus-line pitch are commutative, designing based on any one of them leads to an equivalent (substantially the same) result.

Preferably the optical elements are lenticular lenses. Since there are lenticular lenses with a variety of bus-line pitches, the resultant sheet is of more general applicability.

The optical element layer and the pattern layer have a planar shape, and the pixels each have a linear shape in a direction intersecting with the disposing direction. This configuration leads to a planar-shaped pattern changing sheet with desired dimensions.

The gradation pattern may include a bright part and a dark part. This configuration facilitates the preparation of the gradation pattern.

The gradation pattern may include at least three pixels. With this configuration, at least three-times repetition of the display pattern means the progressing of one wavelength, and so the moving direction is unambiguous.

The walking guidance system according to the present invention includes: the pattern changing sheet as stated above having the speed scale-factor of about 10 times; and a head moving-speed detection unit configured to measure a forward swaying speed of a head above the pattern changing sheet.

This aspect of the present invention effectively induces an initial stepping forward by a patient of a disease, such as Parkinson's disease, during the gait training, and so is suitable for such training and rehabilitation. The condition of the moving speed of the head is preferably about 0.23 m/s to 0.36 m/s, and is more preferably about 0.28 m/s to 0.35 m/s.

What is claimed is:

1. A pattern changing sheet having a display pattern as gradation pattern to be observed from a viewpoint of a viewer, the display pattern progressing at a predetermined speed scale-factor of movement of the viewpoint, the pattern changing sheet comprising:
an optical element layer including optical elements at least in number corresponding to one wavelength of the pattern changing sheet, the optical elements being disposed with a first pitch in a direction orthogonal to an optical axis of the optical elements, each optical element having a light-transmitting part in a plane having a direction of disposing the optical elements and the direction of the optical axis, the light-transmitting part enabling the viewer to view inside of the optical element layer from a plurality of directions intersecting with the optical-axis direction;
a pattern layer disposed on a rear face of the light-transmitting part of the disposed optical elements to be opposed to the optical elements, the pattern layer having a gradation pattern having pixels assigned at positions on the rear face of the light-transmitting part so as to allow the viewer to view the pixels in the plurality of directions from the viewpoint to the optical elements, wherein
the optical element layer and the pattern layer have a planar shape;
the pixels each have a linear shape in a direction intersecting with the disposing direction; and
the display pattern of the one wavelength is expressed based on the pixels in each optical element, each pixel being assigned to a corresponding direction of the plurality of directions, the number of the pixels in the gradation pattern being set at a predetermined number so that, as the viewpoint moves while sequentially changing into an adjacent direction of the plurality of directions, the display pattern at the predetermined speed scale is configured to progress repeatedly a number of times corresponding to the plurality of directions so as to progress by the one wavelength.

2. The pattern changing sheet according to claim 1, wherein the gradation pattern includes a bright part and a dark part.

3. The pattern changing sheet according to claim 1, wherein the gradation pattern satisfies the condition expressed by Expression 1:

$$n = \left\lfloor \frac{W}{L_0^*} \right\rfloor, \; m = \left\lfloor \frac{\Delta W}{L_0^*} \right\rfloor, \; j = \left\lfloor \frac{2\gamma \rho H}{D L_0^*} \tan \frac{\alpha}{2} \right\rfloor \quad \text{(Expression 1)}$$

In Expression 1
dW<W/2, j<n/2;
⌊ ⌋ denotes floor functions;
design values n, m, are integers, and j<n/2, m<n;
W denotes one wavelength at the display pattern;
ΔW denotes the length of the bright part of the gradation pattern;
equivalent bus-line pitch $L_0^* = (1+h/H) \cdot L_0$, and $L_0$ denotes the first pitch;
H denotes a distance from the optical elements to the viewpoint;
h denotes the thickness of the optical elements;
D denotes the resolution;
γ denotes the speed scale-factor;
ρ denotes the density of bus lines; and
α denotes an expected angle.

4. The pattern changing sheet according to claim 1, wherein the optical elements are lenticular lenses.

5. The pattern changing sheet according to claim 1, wherein the gradation pattern includes at least three pixels.

6. A walking guidance system comprising:
the pattern changing sheet according to claim 1, the speed scale-factor being about 10 times; and
a head moving-speed detection unit configured to measure a forward swaying speed of a head of the viewer above the pattern changing sheet.

7. A moving speed reduction device comprising the pattern changing sheet according to claim 1 attached to at least one of a road surface and a road wall.

* * * * *